US012611201B2

(12) United States Patent
Malanowska-Stega et al.

(10) Patent No.: US 12,611,201 B2
(45) Date of Patent: Apr. 28, 2026

(54) ABSORPTIVE TIP BRUSH BIOPSY DEVICE, KIT AND METHOD

(71) Applicants: Zanetta Malanowska-Stega, Southampton, NY (US); Damian Stega, Southampton, NY (US)

(72) Inventors: Zanetta Malanowska-Stega, Southampton, NY (US); Damian Stega, Southampton, NY (US)

(73) Assignee: Techmed Ventures LLC, New York, NY (US)

( * ) Notice: Subject to any disclaimer, the term of this patent is extended or adjusted under 35 U.S.C. 154(b) by 1180 days.

(21) Appl. No.: 17/469,821

(22) Filed: Sep. 8, 2021

(65) Prior Publication Data

US 2023/0073028 A1     Mar. 9, 2023

(51) Int. Cl.
*A61B 10/00* (2006.01)

(52) U.S. Cl.
CPC .. *A61B 10/0045* (2013.01); *A61B 2010/0074* (2013.01)

(58) Field of Classification Search
CPC .................... A61B 10/0045; A61B 2010/0074
See application file for complete search history.

(56) References Cited

U.S. PATENT DOCUMENTS

| | | | |
|---|---|---|---|
| 7,767,448 B2 * | 8/2010 | Yong .................. | A61B 10/0045 600/172 |
| 8,827,923 B2 * | 9/2014 | Vom ......................... | A61F 13/38 600/572 |
| 2009/0306702 A1 * | 12/2009 | Miloslavski ......... | A61B 17/221 604/264 |
| 2011/0087133 A1 * | 4/2011 | Ching .................... | A61B 10/02 600/572 |
| 2017/0367682 A1 * | 12/2017 | Smith .................... | A61B 8/466 |
| 2018/0161021 A1 * | 6/2018 | Malanowska-Stega ..................... A61B 10/02 |
| 2022/0395259 A1 * | 12/2022 | Thakor .............. | A61B 10/0291 |

\* cited by examiner

*Primary Examiner* — Justin Xu

(74) *Attorney, Agent, or Firm* — Hoffberg & Associates; Steven M. Hoffberg

(57)     ABSTRACT

A flexible coaxial tissue sampling device, comprising: a sheath; a displaceable wire within the sheath having a first end extending from a proximal end of the sheath and second end which extends, in a first state, from a distal end of the sheath, and in a second state, retracts into the distal end of the sheath; the second end of the displaceable wire comprising a cellular sampling structure and a porous absorptive material which are external to the sheath in the first state and internal in the second state. A tension on the first end of the displaceable wire at the proximal end of the sheath retracts the displaceable wire from the first state to the second state, along with the cellular sampling structure and the porous absorptive material. The porous absorptive material retains a fluid sample after retraction and protects against contact of the sample with other tissues.

20 Claims, 6 Drawing Sheets

ABSORPTIVE TIP BRUSH BIOPSY DEVICE, KIT AND METHOD

CROSS REFERENCE TO RELATED APPLICATIONS

The present application is a non-provisional of, and claims benefit of priority under 35 U.S.C. § 119(e) from U.S. Provisional Patent Application No. 63/075,728, filed Sep. 8, 2020, the entirety of which is expressly incorporated herein by reference.

FIELD OF THE INVENTION

The present invention provides a system and method for performing a biopsy of the uterus. More particularly, it is a device that disrupts and samples cells from the endometrium, and simultaneously takes a sample with an abrasive brush, an aspirate, and an absorptive structure.

BACKGROUND OF THE INVENTION

Each reference cited herein is expressly incorporated herein in its entirety, for all purposes.

The present technology represents improvements over U.S. Pat. Nos. 9,351,712, 8,920,336, 8,517,956, 8,348,856, and 20180161021. Those patents, in turn, represent an improvement over the Cook Medical Tao Brush™ I.U.M.C. Endometrial Sampler, and the Pipelle endometrial biopsy device (See, Sierecki A R, Gudipudi D K, Montemarano N, Del Priore G., "Comparison of endometrial aspiration biopsy techniques: specimen adequacy." J Reprod Med. 53(10):760-4, 2008 October). See also:

Del Priore, G, R Williams, C B Harbatkin, L S Wan, K Mittal, G C Yang, "Endometrial brush biopsy for the diagnosis of endometrial cancer", Comparative Study J Reprod Med. 2001 May; 46(5):439-43.

Du J, Li Y, Lv S, Wang Q, Sun C, Dong X, He M, Ulain Q, Yuan Y, Tuo X, Batchu N, Song Q, Li Q, "Endometrial sampling devices for early diagnosis of endometrial lesions", J Cancer Res Clin Oncol. 2016 December; 142(12):2515-2522. doi: 10.1007/s00432-016-2215-3. Epub 2016 Aug. 11.

Han L, Du J, Zhao L, Sun C, Wang Q, Tuo X, Hou H, Liu Y, Wang Q, Ulain Q, Lv S, Zhang G, Song Q, Li Q, "An Efficacious Endometrial Sampler for Screening Endometrial Cancer", Front Oncol. 2019 Feb. 19; 9:67.

Kumar A, "Tao Brush", J Obstet Gynaecol India. 2017 August; 67(4):304-305. doi: 10.1007/s13224-017-1006-3. Epub 2017 May 13.

Makem J, Sager F, Bender R (1997). "Endometrial Collection and Interpretation Using the Tao Brush and the CytoRich Fixative System". Diagnostic Cytopathology. 17 (5): 339-346

Suh-Burgmann E, Hung Y Y, Armstrong M A, "Complex atypical endometrial hyperplasia: the risk of unrecognized adenocarcinoma and value of preoperative dilation and curettage", Obstet Gynecol. 2009 September; 114(3):523-9. doi: 10.1097/AOG.0b013e3181b190d5.

Symonds I., "Ultrasound, hysteroscopy and endometrial biopsy in the investigation of endometrial cancer". Best Pract Res Clin Obstet Gynaecol. 2001 June; 15(3):381-91. doi: 10.1053/beog.2000.0183.

Urick M E, Bell D W, "Clinical actionability of molecular targets in endometrial cancer", Nat Rev Cancer. 2019 September; 19(9):510-521.

Williams A, Brechin S, Porter A, Warner P, Critchley H. Factors affecting adequacy of Pipelle and Tao Brush endometrial sampling. BJOG 2008; 115:1028-1036.

Wu H H, Casto B D, Elsheikh™, "Endometrial brush biopsy. An accurate outpatient method of detecting endometrial malignancy", J Reprod Med. 2003 January; 48(1):41-5.

Yang G, Wan L S (2000). "Endometrial Biopsy Using the Tao Brush Method". Journal of Reproductive Medicine. 45 (2): 109-114. PMID 10710740.

Youssif S N, McMillan D L, "Outpatient endometrial biopsy: the pipelle". Br J Hosp Med. 1995 Sep. 6-19; 54(5):198-201.

As shown in FIGS. 3 and 4, the Tao Brush™ has a bead at the tip, to reduce trauma when the brush reaches the fundus of the uterus. FIG. 4 shows the brush extended from the sheath, while FIG. 2 shows the brush retracted. Proximal to the brush, on the guidewire, is an inner sleeve provided to center the wire, but this does not provide an interference fit, and does not draw a vacuum when the guidewire is retracted. The sample taken by the Tao Brush™ represents the cells swept or abraded from the endometrium, by the bristles. See also, U.S. Pat. Nos. 3,774,590; 3,877,464; 3,881,464; 4,108, 162; 4,227,537; 4,235,244; 4,641,662; 4,662,381; 4,754, 764; 4,763,670; 4,966,162; 5,092,345; 5,146,928; 5,217, 024; 5,253,652; 5,279,307; 5,328,826; 5,462,063; 5,535, 756; 5,546,265; 5,713,369; 5,857,982; 5,916,175; 5,931, 845; 5,954,670; 6,059,735; 6,132,421; 6,258,044; 6,336, 905; 6,494,845; 6,572,578; 6,610,005; 6,676,609; 6,730, 085; 6,913,921; 7,004,913; 7,541,161; 7,749,173; 7,767, 448; 7,906,076; 8,048,669; 8,097,429; 8,152,739; 8,251, 918; 8,323,211; 8,329,474; 8,348,856; 8,439,847; 8,517, 956; 8,652,067; 8,778,670; 8,795,197; 8,827,923; 8,920, 336; 8,968,213; 8,969,075; 9,044,213; 9,046,522; 9,078, 642; 9,282,951; 9,351,712; 9,393,394; 9,447,467; 9,541, 477; 9,687,642; 9,820,722; 9,895,140; 10,149,666; 10,201, 332; 10,258,780; 10,576,248; 10,736,615; 10,631,835; 10,028,769; 9,913,629; 9,820,722; 9,730,679; 9,655,600; 9,351,712; 8,920,336; 8,517,956; 8,348,856; 6,733,962; 6,572,578; 6,491,645; 6,371,973; 6,086,546; 6,042,552; 5,951,490; 5,810,861; 5,807,282; 20200221932; 20200033351; 20190282071; 20190233893; 20190142399; 20180193006; 20180161021; 20180110501; 20180049729; 20170367682; 20160128728; 20160032392; 20150088032; 20140039346; 20140024557; 20130022593; 20110171631; 20090240164; and U.S. Pat. No. D658,388.

Sampling devices for cervical tissue are disclosed in US 20160331357 and 20020161313. Cervical sampling differs from endometrial sampling in that the cervix and the cervical os, are more accessible, and that to obtain a proper sample of endometrial tissue, the biopsy device must be protected as it passes through the cervix. Further, the diameter of the endometrial biopsy device is constrained by the cervical os.

FIGS. 20A-20C and 7 show the use of the Tao Brush™. The manufacturer (Cook Medical) provides the following instructions for use:

1. Position screw-cap test tube containing 8 ml of CytoRich® Brush Cytology Preservative (AutoCyte, Inc., Elon College, NC) in a test-tube rack at the site of the procedure.
2. Place patient in lithotomy position.
3. Retract the brush sampler completely into the outer sheath.
4. Gently insert the device to the level of the fundus. (FIG. 20A)
5. Pull back the outer sheath all the way to the handle. Amply rotate the brush sampler. (FIG. 20B)

6. In order to trap endometrial material in situ, push the outer sheath over the brush to the tip and remove the device. (FIG. 20C). The normal endometrial cavity is in a collapsed state, so the brush will have direct contact with the entire endometrial surface.

7. Immediately immerse the device into 8 ml of CytoRich® Brush Cytology Preservative. (FIG. 7)

8. Retract the sheath to expose the brush to preservative solution.

9. Hold the sheath firmly and move the brush in and out of the sheath to clean it of adherent cells and tissue. Collections are generally stable in preservative for periods of up to several weeks.

10. Remove the brush assembly from the test-tube, replace the screw cap, and submit the tube to the laboratory for processing.

Two alternate methods of obtaining the biopsy sample are suggested:

1) Rotate brush sampler in a clockwise manner until reference mark on the handle indicates completion of a 3600 turn, then rotate counterclockwise the (opposite direction) until the reference mark on the handle indicates completion of a 360° turn;

2) Rotate the brush sampler in only one direction by completing 4 or 5 360° rotations. Note: Reference mark on handle indicates completion of a 360° rotation.

To Obtain Uncontaminated Endometrial Cultures

1. After insertion of a sterile, nonlubricated vaginal speculum, swab the ectocervix and the endocervical canal with povidone iodine solution. NOTE: Insert the swab about 1.5 cm into the endocervical canal to ensure adequate swabbing of the endocervix with the povidone.

2. Insert the brush into the endometrial cavity following steps 3-6 from the section preceding these instructions. The reference mark on the handle indicates completion of a 3600 turn.

3. Remove sampler.

4. Wipe the rounded tip of the brush with 95% alcohol gauze.

5. Pull back the sheath. Prepare morphologic evaluation (if required) by preparing a direct smear on a sterile glass slide and spray-fix immediately.

6. For culture studies, place the brush into sterile Stuarts Transportation Medium and agitate for 5 seconds.

FIGS. 8A (before sample) and 8B (after sample is drawn) show a Pipelle biopsy tool, which aspirates a sample into a sheath, but does not have an exposed brush.

FIGS. 9 and 10A-10C show the design according to U.S. Pat. Nos. 9,351,712, 8,920,336, 8,517,956, and 8,348,856, which improve the Tao Brush™ design by implementing an aspiration biopsy in addition to an abrasive tissue sampling biopsy. This is achieved by providing an interference fitting plunger 4 proximal to the biopsy brush 3, which draws in a fluid sample from the uterus as the brush is withdrawn into the sheath 1 by withdrawal of the wire 2. FIG. 10A shows the brush in the initial state during insertion into the uterus. FIG. 10B shows the brush extended from the sheath. FIG. 10C shows the brush withdrawn into the sheath after a biopsy sample is taken.

However, according to the Tao Brush™ design and that of U.S. Pat. Nos. 9,351,712, 8,920,336, 8,517,956, and 8,348, 856, the brush is inserted either an arbitrary or estimated distance, or until resistance is encountered by the tip of the brush pushing against the fundus of the uterus, which risks unnecessary tissue damage, and in some cases, complications.

U.S. Pat. Nos. 9,351,712, 8,920,336, 8,517,956, and 8,348,856 discuss an intrauterine biopsy sampling device having a narrow cylindrical tube with a guidewire and biopsy sampling device at the end at the end of the guidewire, similar to a Cook Medical (Bloomington, IN) Tao Brush™ I.U.M.C. Endometrial Sampler, modified such that disposed within the sheath, is a piston-like structure which, when the wire is withdrawn through the sheath, draws a vacuum and sucks fluid surrounding the guidewire into the sheath. A vacuum biopsy sampling device, such as the known Pipelle endometrial suction curette, produces a vacuum and draws it into the sheath by a similar principle, but lacks the brush or other biopsy sampling device at its distal end.

The device as shown in FIG. 9, is a 1-3 mm diameter by 30-40 cm long coaxial "straw" or sheath 1 that can easily pass into the uterus endometrial cavity with little or no discomfort. It is malleable but rigid enough to apply sufficient force to pass through the cervix. In the center of the sheath 1, which is an impermeable tube, a thinner inner insert guidewire 2 can be extended beyond the end 3 of the sheath into the uterus. Proximal from the biopsy brush 5 is a suction element 4, which draws liquid into the sheath 1 when the guidewire 2 is withdrawn. The brush 5 disrupts the uterus to loosen and collect a biopsy sample of the uterus. The tissue sampling device includes a spirally twisted flexible guidewire 2 with opposed proximal and distal ends. Also included is the sheath 1 which is a plastic tube 7 (shown in FIG. 11) covering a significant portion of the guidewire 2 to provide additional rigidity without making the overall biopsy sampling device stiff.

Along the distal end portion of the guidewire 2 is a brush 5 that includes bristles that were used for collecting a tissue sample. The bristles are fixed within the spirally twisted guidewire 2 near the distal end and are tapered from smaller to larger towards the distal end of the guidewire 2. Tapering of the bristles from the distal end of the device allows for more global tissue collection of the endometrium because of the shape of the endometrial cavity. An atraumatic bulb 6 (shown in FIG. 11) is located on the extreme distal end of the twisted guidewire 2. The plastic tube 7 and twisted guidewire 2 are contained within the sheath 1 having a shorter length than the twisted guidewire 2, such that the sheath 1 can be moved along the plastic tube 7 to the atraumatic bulb 6 on the distal end of the twisted guidewire 2, thereby covering the brush 5 during insertion and removal after tissue collection.

Before insertion, the sheath 1 can be moved into position over the distal end of the twisted guidewire 2 to protect the brush 5 during insertion. Having the brush 5 covered during insertion also increases comfort for the patient and protects the brush 5 from collecting tissue from unintended areas. The sheath 1 is moved back toward the proximal end of the twisted guidewire 2 after the device has been inserted to the proper collection depth, exposing the brush 5 and allowing for collection of a tissue sample. The sheath 1 may be moved to completely uncover the brush 5 or may be moved in gradients to uncover portions of the brush 5. This allows the practitioner to adjust the effective collection area of the brush 5 based on the anatomy of the patient.

The plastic tube 7 covering the guidewire 2 is scored 8 in centimeter gradations along the plastic tube 7 with markings indicating the exact length of the brush 5 inserted into the uterus, starting from the distal tip of the brush 5 to the proximal end 3 of the sheath 1. This allows the clinician to know how deeply the brush 5 is inserted into the uterus. The sheath 5 is approximately the same length as the plastic tube 7 and in position to cover the brush 5 bristles prior to insertion. The sheath 1 may be formed of a clear material such that the gradations 8 on the plastic tube 7 may be viewed through the sheath 1. The ability to measure insertion depth increases the certainty that the tissue sample collected is from the correct area. After a tissue sample is collected from the proper area, while the tissue sampling device remains inserted, the sheath 1 can be moved back along the distal end of the twisted guidewire 2 to cover the brush 5 bristles before removing the brush 5. This allows for the tissue sample to be protected on the brush 5 within the sheath 1 during removal.

Additionally, the gradations 8 along the flexible plastic tube 7 allow the practitioner to measure the length of brush 5 bristles exposed. As the practitioner pulls the sheath 1 from its insertion position towards the handle 9 (shown in FIGS. 5 and 6), the further the sheath 1 is pulled the more bristles of the brush 5 are exposed. The gradations 8 (ruler) provide a visual confirmation of this measurement and allow the practitioner to be precise in exposing only a certain length of the brush 5 bristles. This measurement allows the practitioner to have better control of where the tissue is sampled and allows the practitioner to adjust the length of brush 5 based on patient specific parameters; such as uterine size measured during previous tests or inferred based on patient history. Control of brush 5 exposure increases sampling precision and patient comfort.

Simultaneously with withdrawal of the brush 5 back into the narrow cylindrical tubular sheath 1, the device creates a weak suction with the suction element 4 to collect the disrupted sample into the sheath 1. The entire apparatus is then withdrawn from the uterus and the sample is collected by reversing the process outside the body.

Combining two or more biopsy methods into one device eliminates pain, discomfort, and inconvenience, e.g., a second procedure to obtain an adequate and accurate specimen. The multiple methods of specimen collection, e.g., disruption by physical means, and suction, used together, allows a gentler application of the individual methods, e.g. a gentle disruption and gentle suction applied simultaneously can replace a vigorous disruption, e.g. D&C, and a powerful suction. The combination of multiple gentler methods in one device is safer and more effective than any method alone. See:

Borja J M, Galindo P A, Gomez E, Feo F. Contact dermatitis due to povidone-iodine: allergic or irritant?. J Investig Allergol Clin Immunol 2003; 13(2):131-2.

Dijkhuizen F P, Mol B W, Brolmann H A, Heintz A P. The accuracy of endometrial sampling in the diagnosis of the patients with endometrial carcinoma and hyperplasia: a meta-analysis. Cancer 2000; 89(8):1765-72.

Feldman S, Berkowitz R S, Tosteson A N. Cost-effectiveness of strategies to evaluate postmenopausal bleeding. Obstet Gynecol 1993; 81(6):968-75.

Ferry J, Farnsworth A, Webster M, Wren B. The efficacy of the pipelle endometrial biopsy in detecting endometrial carcinoma. Aust N Z J Obstet Gynecol 1993; 33:1-76.

Grimes D A. Diagnostic dilation and curettage: A reappraisal. Am J Obstet Gynecol 1982; 142:1-6.

Guido R S, Kanbour-Shakir A, Rulin M, Christopherson W A. Pipelle endometrial sampling: sensitivity in the detection of endometrial cancer. J Reprod Med 1995; 40:553-5.

Huang G S, Gebb J S, Einstein M H, et al. Accuracy of preoperative endometrial sampling for the detection of high-grade endometrial tumors. Am J Obstet Gynecol 2007; 196:243.e1-243.e5.

Kozuka T. Patch testing to exclude allergic contact dermatitis caused by povidone-iodine. Dermatology 2002; 204 Suppl 1:96-8.

McCluggage W G. My approach to the interpretation of endometrial biopsies and curettings. J Clin Pathol. 2006; 59:801-12.

Naim N M, Mahdy Z A, Ahmad S, Razi Z R M. The Vabra aspirator versus the pipelle device for outpatient endometrial sampling. Aust N Z J Obstet Gynecol 2007; 47(2): 132-6.

Ong S, Duffy T, Lenehan P, Murphy J. Endometrial pipelle biopsy compared o conventional dilatation and curettage. Ir J Med Sci 1997; 166:47-9.

Phillips V, McCluggage W G. Results of a questionnaire regarding criteria for adequacy of endometrial biopsies. J Clin Pathol. 2005; 58:417-9.

Ries L A G, Melbert D, Krapcho M, Mariotto A, Miller B A, Feuer E J, Clegg L, Homer M J, Howlader N, Eisner M P, Reichman M, Edwards B K (eds). SEER Cancer Statistics Review, 1975-2004, National Cancer Institute. Bethesda, MD, seer.cancer.gov/csr/1975_2004/, based on November 2006 SEER data submission, posted to the SEER web site, 2007.

Stovall T G, Photopulos G J, Poston W M, Ling F W, Sandles L G. Pipelle endometrial sampling in patients with known endometrial carcinoma. Obstet Gynecol 1991; 77:954-6.

Tahir M M, Bigrigg M A, Browning J J, Brookes S T, Smith P A. A randomized controlled trial comparing transvaginal ultrasound, outpatient hysteroscopy and endometrial biopsy with inpatient hysteroscopy and curettage. Br J Obstet Gynecol 1999; 106(12):1259-64.

Van den Bosch T, Vandendael A, Wranz P A, Lombard C J. Endopap-versus Pipelle-sampling in the diagnosis of postmenopausal endometrial disease. Eur J Obstet Gynecol Reprod Biol 1996; 64:91-4.

Yang G C, Wan L S, Del Priore G. Factors influencing the detection of uterine cancer by suction curettage and endometrial brushing. J Reprod Med 2002; 47:1005-10.

SUMMARY OF THE INVENTION

The present invention provides multiple sampling modalities for intrauterine tissue biopsy. First, there is a brush or tissue surface disruptive modality. Second, there is a bulk fluid and suspended cellular material sampling modality. Third, there is a fluid absorptive modality. These features may be provided in combination or subcombination.

A preferred embodiment of the present invention provides a narrow cylindrical tube with a guidewire and biopsy sampling device at the end, similar to a Cook Medical (Bloomington, IN) Tao Brush™ I.U.M.C. Endometrial Sampler, modified such that the distal tip of the biopsy sampling device has an absorptive structure which draws in cellular material. Further, proximal to the biopsy sampling device on the guidewire is a flange or piston structure, that draws a vacuum in the tube as the guidewire is withdrawn at the conclusion of sampling.

Surrounding the cylindrical tube, a cervical stop may be provided that limits insertion of the cylindrical tube beyond a fixed distance past the external os of the uterus. The cervical stop may be adjustable along the cylindrical tube to control depth. Optionally, the movement of the cervical stop on the cylindrical tube may be limited in range, to be positioned at the cervix at initial insertion, and then provide tactile feedback when the cylindrical tube is fully inserted. Therefore, the user can control both the extension of the biopsy sampling device from the end of the cylindrical tube, and the depth of insertion of the cylindrical tube into the uterus. This additional parameter is meaningful since the sample drawn by the brush, and especially by the flange or piston, will depend on where the opening of the cylindrical tube is when the biopsy sampling device is withdrawn into it. See, U.S. Pat. Nos. 9,351,712, 8,920,336, 8,517,956, and 8,348,856.

For example, the cervical stop may have a frictional fit with the cylindrical tube to provide damped but smooth axial movement. At the ends of the range, a proximal and distal protrusion or O-ring may be provided, to limit the sliding movement. Alternately, the smoothness or frictional coefficient of the cervical stop against the cylindrical tube may abruptly change, especially in the distal case. Indeed, sequential zones of frictional variation (e.g., every centimeter) may be provided to provide haptic/sensory feedback to the user to permit counting of the depth of insertion. When the cervical stop reaches the proximal stop, that will limit further insertion to help avoid puncturing the uterus with the end of the biopsy sampling device.

For sampling, the biopsy sampling device (e.g., brush) is withdrawn into the cylindrical tube by retracting the guidewire while maintaining the insertion depth of the cylindrical tube, which then samples fluid surrounding the biopsy sampling device at that position by drawing a vacuum from the retraction of the flange or piston structure. Therefore, the cylindrical tube should be inserted to the desired depth from where the fluid surrounding the biopsy sampling device is desired to be sampled. Unless a restraining force is applied to the cervical stopper, when the cylindrical tube is withdrawn from the uterus, the cervical stopper will no longer contact the cervix.

The biopsy sampling device may extend a few centimeters beyond the end of the cylindrical tube during the procedure, before being withdrawn back into the cylindrical tube and withdrawal from the cervical os.

The distal protrusion or O-ring is inserted into the cervical os, and must therefore not cause tissue trauma. The proximal protrusion or O-ring is not inserted into the cervical os, and remains proximal to the larger cervical stop.

The distal protrusion or O-ring may be fixed or displaceable, and in some cases, the user may wish to adjust the initial depth of insertion.

As mentioned above, the distal tip of the biopsy sampling device includes a porous absorptive structure, that can draw a cellular fluid sample from the endometrium. The tip also includes an atraumatic function which caps the end of the guidewire (if it extends that far) and prevents puncture of the endometrium by the biopsy sampling device. The porous absorptive structure is preferably frictional or textured, to provide abrasive quality to shear off cells from the surface, while the biopsy sampling device is being manipulated. For example, a polymeric foam bulb may be formed over a cap on the end of the guidewire, distal to a set of bristles that extend from the guidewire, which in turn is distal to the flange or piston structure. The foam bulb in this case is adhered to the cap, and is sized and configured to be withdrawn into the cylindrical tube so that the porous absorptive structure is isolated from the cervix during insertion and withdrawal. Likewise, this protects the porous absorptive structure from compression and consequent loss of sample during withdrawal.

The sample(s) obtained by the device are preferably suitable for genetic material analysis, i.e., PCR or RT-PCT for DNA and RNA, respectively. In order to avoid contamination, it is preferable that the materials, especially the foam or other absorptive material, be synthetic and sterile.

The device is intended to collect tissue samples from the lining of the uterus (endometrium). The device has a brush at the distal end of the catheter. The brush is intended to gently sample the endometrium by brushing off surface mucous and cells. The proximal end of the device has a handle for ease of physician handling. The device has a relatively rigid, outer sheath, that can be move along the length of the device (with respect to the handle), to cover or expose the brush at the distal end.

The device preferably has a skirt stopper, i.e., the cervical stop, around the distal end of the outer sheath. A skirt stopper is preferably an annular flange which extends radially from a hub around the cylindrical sheath. The skirt stopper may be formed of a flexible silicone or polyurethane rubber.

The skirt is intended to locate the device in relation to the cervix. The cervical stop may be fixed in position, i.e., displaced from the tip a sufficient amount to permit the end of the cylindrical tube to be inserted past the cervical epithelial cells, or manually slidable along the outer sheath. In general, the cervical stop, if slidable, should have a sufficiently frictional coefficient with respect to the outer surface of the cylindrical tube, to remain axially fixed in position after placement except where intentionally repositioned, such that when the cervical stop abuts the cervix, manipulation of the guidewire and the sheath will not unintentionally reposition the cervical stop.

A series of axial markings are preferably provided to allow quantitative alignment of the cervical stop along the sheath. As noted above, a marking may also be provided showing the user a degree of rotation of the guidewire with respect to the cylindrical tube.

In some cases, portions of the biopsy process may be automated. For example, one or more electrical motors may control the rotation and extension of the guidewire. For example, a coreless DC motor (e.g., type 0408, 0412, or 612) motor may drive guidewire rotation through e.g., a reducing gear transmission, while a similar motor may be operated as a servo to control extension and retraction from the sheath. For example, the worm gear and follower (screw and nut) may be used. The control may be an ARM MO or M4-based microcontroller, executing Arduino or other operating system, or directly microcoded. Advantageously, the processor is included within an RFID device, to provide both identification and information processing functions, and control functions, e.g., NXP PN7462, NTAG203; NTA53321G0F, etc.

The control is preferably reusable, while the biopsy catheter is preferably single use, and transported to the pathology lab for analysis. The control is preferably autoclavable, or gas sterilizable, though it may also be waterproof and sterilized and/or cleaned by immersion into a sterilization/antiseptic solution. The microcontroller and power supply may be wirelessly coupled to the motor/actuator unit, for example coupled through a Qi or other wireless standard inductive coupling. As discussed below, other automated functions are possible using electronic assistance, and the basic sampling functions for a single biopsy device are reasonably performed manually by a skilled user without electronics.

The skirt stopper is preferably made of an elastomer with rounded edges, such as rubber, silicone, or plastic, having sufficient elasticity to provide the desired characteristics and avoid unintended traumatic injury even when a user applies excess pressure.

The device is intended to be advanced into the patient with the brush covered by the outer sheath until the skirt encounters the cervix and can advance no further. After the skirt is stopped against the cervix, the brush is advanced past the end of the sheath by moving the guidewire with respect to the sheath, to expose the brush inside the uterus, to allow tissue sampling. The skirt provides a force on the sheath when pressed against the cervix.

The device also has an O-ring, flange or piston secured to the main shaft, i.e., guidewire, of the catheter. The outer sheath, i.e., the cylindrical tube and O-ring, flange or piston create a seal against each other, and create suction (vacuum) at the distal end of the catheter for securing tissue samples when the guidewire and brush are withdrawn into the sheath.

The device is removed from the patient with the brush covered by the outer sheath. A stop may be provided to limit withdrawal of the guidewire into the sheath. For example, a toroidal or cylindrical member attached in fixed position inside the sheath may interfere with the O-ring (or flange or piston), and thus limit retraction.

The device preferably sterile, and intended for single-use only. Advantageously, the guidewire and sheath may be readily cut with a scissors (shears) or wire cutter, to reduce the material that need be transported for analysis. A cut point may be provided, which is more easily severed than the remainder. Typically, a twisted or braider stainless steel guidewire will be difficult to cut, or will scar a fine scissor. However, a weak portion of the wire may be provided, either my modifying the wire in a weak region, or providing an insert.

While a bar code or 2D bar code may also be used for identification, a writable RFID device has the advantage of being readable without being visible (e.g., cloaked or sheathed), being readily updatable during use (writable tags), avoids requirement of a line of sight, and permits cryptographic authentication and access limitations (depending on selected integrated circuit). In some cases, identity and associated information may be stored on a blockchain or distributed blockchain, which avoids need for centralized access on one hand, and avoids single point of failure and implicit trust on the other. Thus, using cryptographic handshaking, an RFID device associated with the biopsy device, for example, embedded in the manipulation handle or cervical stop, can store identifying information, which may be a mere index number, or programmed with specific patient identification, as well as ad hoc or structured information, such as procedure and reporting details. In some cases, the preferred standard for the RFID may be according to ISO 11784 and ISO 11785, which operate at lower frequencies than ISO 14443, and thus may use a ferrite antenna with a coil wrapped around it, facilitating a cylindrical form factor and placement in, or molding within, the handle.

In some cases, the handle is severed (cut) from the handle to facilitate transport to the lab for analysis, and analysis. In that case, if the RFID is in the handle, it will be separated from the associated sample. In that case, the RFID may be provided on the sheath. An RFID semiconductor device is typically less than 2 mm, and potentially less than 1 mm, and so may be mounted on the sheath. However, the RFID antenna is generally configured as a coil around an area. In this case, the antenna may be long and thin, and wrapped around the sheath. For example, the antenna may be embedded in the sheath, or additively printed on its surface.

The identification may also be a linear bar code on the sheath, or a QR code on the handle or tag associated with the handle end of the device. This may be printed or laser inscribed.

According to another embodiment, the identification is provided on a sample collecting chamber (cup) into which the collected sample, i.e., the brush, sponge tip, and fluid withdrawn into the sheath, is placed after biopsy. In that case, the RFID may be a module inside the sample collecting container, outside the sample collecting container, or embedded in the wall or top of the sample collecting container. The sample collecting container may have a pocket for retaining the brush inside it. The sample collecting container may be prefilled with a preservative and/or fixative solution. Typically, the tip of the biopsy device is severed before placement into the sample collection container. The pocket may be securely closed about the tip, to prevent reopening outside of the pathology lab without evidence of tampering. Alternately, the pocket may have a reopenable flap closure.

The sponge tip has limited fluid absorption and therefore when withdrawn into the sheath, is not squeezed to discharge its fluid payload. For example, expansion of the sponge when absorbing fluid may be 0-30%. For example, absorption may be largely by capillary action rather than expansion.

In some cases, the RFID is separable from the biopsy device, and is manually transferred with the tip to (or in conjunction with) the sample collecting container.

Alternately, the RFID device may act similarly to a contactless RF credit card, e.g., according to NFC (en.wikipedia.org/wiki/Near-field_communication) or other standard, such as ISO/IEC 14443. Instead of storing the information in the device, the device provides secure authentication for itself, which links to a record which then is access based on proof of authenticity of the device, based on a cryptographic handshake. Access to confidential information may then require that the subsequent user, which is e.g., at the pathology lab, have verified credentials. For example, a physician who takes a sample may program the patient record for a specific lab. Alternately, a lab may provide its biopsy devices to physicians, and only it can then read and use the electronically stored information using a private key or PIN.

The biopsy device may have a writable RFID device, and the information written may be encrypted or cryptographically protected. The need for RFID arises from avoidance of contact, which in the case of biopsy specimens, may be associated with biohazards and contamination. On the other hand, RFID allows reading and writing of tags without breaching a sanitary or sealed enclosure. The writable RFID device may include various relevant parts of the procedure record and/or the patient record, though prudence dictates that the information stored should be curtailed to that required or reasonably relevant for the analysis and reporting of the biopsy device. In some cases, the biopsy device is stored after receipt, for example it may include forensic evidence, and in that case, it may be advantageous for the tag to include chain of custody, storage conditions, and the like, which can be updated or automatically updated after initial sampling.

In accordance with another embodiment of the invention, a multiple sample biopsy device is provided, capable of obtaining and segregating a plurality of biopsy samples taken in a single session. In accordance with this embodiment, the biopsy instrument is placed at an anatomical orifice, such as a cervical os or anus. Advantageously, a protrusion provides a positional reference with respect to the outer portion of the orifice, similar to the aforementioned cervical stop. This protrusion may be part of the design, or an added element to achieve the desired depth-of-insertion reference function.

The multiple sample biopsy device may advantageously be automatically controlled with an electronic microcontroller. In this case, the selection and actuation of the multiple sample components may be automatic, controlled by a microcontroller. Similarly, in some cases, the biopsy sampling may benefit from automated control. For example, the collection of different isolated liquid specimens during a procedure may entail a controlled vacuum source, and sample isolation. The samples may also be electronically labelled and identity managed based on an electronic or RFID tag.

The biopsy device according to the multiple sample embodiment provides a plurality of biopsy sampling tools, which may each be the same or different, e.g., an endocervical sampler, an endometrial sampler, a punch sampler, and an endometrial sampler with suction. Each tool is provided as a device inside a sheath, such as a 1.5-4 mm tube, which is operable by a guidewire to extend the tool sampling head beyond the end of the sheath, twist with respect to the sheath, and retract the tool sampling head back within the sheath.

In addition to providing control over advancing the biopsy tool with respect to the sheath, each sheath is controllable to be selectively inserted into the orifice, and advance into the organ with the biopsy tool retracted into the sheath, and to be removed from the organ with the biopsy tool retracted into the sheath.

In some cases, the sheath itself may be articulable or angularly guidable to direct the biopsy tool to a desired region. The articulable sheath may be a single axis, i.e., a curvature of the end of the sheath, typically as a result of a tension on a tensile element such as cable, guidewire or filament attached to the wall of the sheath. A shape memory alloy (SMA), such as titanium-nickel alloy, may be used as a thermally-controlled actuator. The temperature may be controlled ohmic heating with a control current. By controlling the angle of curvature, and the rotational angle of the sheath with respect to the organ, a reasonable range of control is provided. The SMA elements may be selectively provided at positions along the length of the sheath, and actuated by a signal along a serial control line, which is received by an addressable serial receiver integrated circuit embedded in the sheath. Multiple receivers may be provided, thus providing possibility of complex motions.

Similarly, a punch, or snare, or encapsulating biopsy device may also be controlled by a tension, which may be a wire or polymer filament, or SMA actuator. The case of a single guidewire with a single degree of freedom (advance/retract) is a simplest case, but additional controls and degrees of freedom may be provided.

In some cases, "blind" sampling may be accomplished, for example within a short canal, or at a distal portion of the organ with respect to the orifice.

In other cases, e.g., within a lumen of a larger organ, some imaging guidance is preferred. Therefore, the device may be used with an endoscope, and/or include an endoscopic camera, such as a 1-3 mm endoscopic camera. Typically, such devices rely on fiber optics from the tip to the imager, for both illumination and imaging. However, according to one embodiment of the technology, the imager circuit and lens are present at the tip of the scope, which in turn is disposed proximate to the end of the biopsy sampling device, to provide direct and real-time imaging of the biopsy procedure.

For example, On Semiconductor provides various suitable devices, such as the MT9V115 1/13" VGA, OV6922 1/18" 1/4 VGA imager, and OVM6946 1/18" 400×400 imager, which may be included as part of a subminiature module that transmits the image as a data stream over an electrical interconnection (or wirelessly). The imager is typically provided with a field of view facing the biopsy tool, with a set of LEDs, or LED illuminated fibers, illuminating the field. While the camera is not required in all modes of operation, i.e., all sampling procedures, if provided, it may remain inserted into the orifice throughout the procedure. The camera may be present near the end of the sheath and advanced with the respective sheath of the biopsy tool into the organ during the procedure. The control for electronics including imaging functions and/or network communications may be based on a Linux or real-time Linux controller, and for example may include or be similar to a Raspberry Pi 4, ESP32, or other known controller or multi-core controller. Typically, a medical device will not employ consumer-grade devices or operating systems, unless no harm can come to the patient from aberrant operation of the device. In the case of a biopsy device, harm is possible, and therefore secure hardware and software is preferred, with code and peripheral device authentication. See, U.S. Pat. Nos. 7,467,370; 7,529, 946; 7,721,096; 7,774,619; 7,849,312; 7,940,934; 7,987, 356; 8,074,287; 8,108,641; 8,261,072; 8,332,653; 8,335, 931; 8,375,221; 8,468,244; 8,468,361; 8,478,973; 8,539, 587; 8,627,414; 8,683,215; 8,725,123; 8,775,757; 8,812, 804; 8,832,465; 8,873,747; 8,997,192; 9,043,632; 9,047, 471; 9,075,995; 9,177,153; 9,189,605; 9,189,653; 9,202, 061; 9,202,082; 9,363,481; 9,367,688; 9,419,794; 9,432, 196; 9,438,424; 9,489,512; 9,514,317; 9,558,330; 9,560, 078; 9,578,008; 9,594,927; 9,667,425; 9,742,790; 9,747, 220; 9,756,037; 9,785,801; 9,842,212; 9,852,305; 9,864, 859; 9,923,755; 9,940,456; 9,980,146; 9,990,479; 10,055, 556; 10,069,633; 10,074,223; 10,083,304; 10,091,195; 10,103,889; 10,110,411; 10,114,935; 10,129,035; 10,135, 619; 10,149,156; 10,154,011; 10,169,574; 10,176,310; 10,218,711; 10,237,070; 10,263,790; 10,268,811; 10,268, 844; 10,270,591; 10,270,748; 10,346,619; 10,366,237; 10,367,840; 10,380,346; 10,390,222; 10,397,280; 10,437, 985; 10,496,811; 10,496,841; 10,567,359; 10,572,650; 20060090084; 20060107032; 20060117177; 20060288238; 20070130472; 20070174616; 20070180271; 20070192604; 20070226496; 20070226787; 20070294181; 20070294496; 20090254572; 20090300366; 20090319782; 20090327741; 20100250497; 20120084438; 20120147937; 20120185680; 20130031374; 20130159729; 20130254906; 20130269012; 20130347058; 20140075567; 20140082352; 20140258700; 20140283138; 20140289794; 20140289833; 20150032946; 20150032951; 20150033038; 20150195276; 20150347768; 20150379306; 20160036826; 20160048678; 20160070932; 20160080325; 20160085916; 20160092877; 20160125187; 20160171248; 20160180061; 20160180068; 20160180078; 20160188848; 20160188853; 20160226913; 20160232105; 20160232108; 20160234019; 20160255097; 20160283703; 20160337329; 20160373474; 20170005790; 20170048070; 20170094510; 20170099604; 20170140153; 20170142163; 20170161501; 20170169231; 20170228554; 20170243012; 20170244565; 20170250892; 20170330187; 20180025183; 20180034682; 20180039795; 20180039990; 20180041341; 20180041503; 20180096137; 20180097639; 20180131687; 20180159880; 20180189482; 20180191501; 20180191695; 20180204399; 20180212814; 20180219841; 20180260570;

20180341756; 20180375666; 20190058625; 20190073479; 20190081803; 20190132739; 20190164156; 20190222424; 20190243949; 20190245696; 20190253404; 20190278919; 20190347432; 20190356529; 20200028868; and 20200028880.

Advantageously, a video signal from an imager may be carried using the guidewire(s) which control the biopsy tool as electrical power and/or signal carriers. Note that the operating voltage is typically low, e.g., <3.3V, so a dangerous condition for the patient would not typically be present in case of electrical leakage. However, the power carrying members may be insulated to further reduce risk and enhance signal integrity. A wireless transmission may also be provided, for example to a nearby wireless receiver, avoiding the need for wired transmission. In that case, the device may have a self-contained battery, receive operating power over a conductor which advantageously may include the guidewire, or received power through indictive coupling. Since the preferred guidewire is multi-stranded, power and ground, and even signal, may be transmitted if the strands are mutually insulated. There is no compelling reason why a guidewire needs to be uninsulated, so this permits enhanced use of an existing structure, at low added cost and complexity. The tip of the device may include LED lighting. Indeed, in some cases, a fluorescent dye which selectively highlights suspect tissue may be employed, and a UV LED used to fluoresce the dye, to reveal areas that should be particularly sampled. In some cases, the dye is a UV activated therapeutic agent. In that case, the biopsy component of the catheter is optional.

The biopsy device according to one multiple biopsy sample embodiment provides a barrel cartridge with the various biopsy tools in angularly displaced positions, or a linear or rectangular array of biopsy tools. One way to selectively activate certain tools is to provide the barrel with a single active position, in which the manipulator controlled by the user provides functional control over a single one of the plurality of biopsy tips, e.g., extension and retraction of the sheath, and extension, retraction and rotation of the guidewire. As discussed above, a function for articulation of the sheath by tension on another actuation filament may also be provided. The remaining biopsy tools in the barrel may remain restrained in their undeployed positions, e.g., clamped in position. Therefore, the number of degrees of freedom for the actuator may be limited to the maximum required by any single tool, plus tool selection.

Because the barrel or array has a larger dimension than the minimum sheath diameter for a single tool, the barrel or array is maintained outside of the organ orifice, and a mechanism for engaging and disengaging each respective biopsy tool is also outside the organ orifice, which, for example, may rotate into position to release one tool while locking the others in retracted position. Thus, a relatively large array (circular or in a spatial array), e.g., 4-20 mm, may be provided with 2-30 biopsy tools in reserve. The end of the barrel or actuator mechanism advantageously serves as the cervical stopper, to limit insertion distance of the sheath into the organ, e.g., uterus, and provide a well-defined positional reference.

According to one embodiment, each biopsy tool in the device is separate (i.e., has a distinct predetermined guidewire actuator), with no changeover in control. Thus, for a biopsy device with four deployable biopsy tools, there are four separate sheaths with respective guidewires extendable from the cartridge. This permits a physician to select the appropriate biopsy tools for a respective procedure, from generic or custom designs. The unused tools remain outside of the organ, while an active tool is in use. In some cases, multiple tools may be advanced into the organ, for example where an endoscope is provided as one of the available tools, and not linked to a particular or single biopsy tool.

On the other hand, in a second embodiment, a mechanism may be provided to mechanically separately engage e.g., the sheath, guidewire, and articulation wire for each separate biopsy tool, with a single control system extending from the cartridge which includes the multiplexed biopsy control paths, we well as an additional biopsy tool selection path. For example, a multi-way clamp, bayonet socket, quick-release, SMA actuator, or magnetic mechanism may be provided to individually engage the respective biopsy tool in the active position. The cartridge is typically round, and centered at the orifice during the procedure, so that the non-deployed biopsy devices are eccentric within the cartridge when not in use. As they are brought into the active position, such as by rotation of a lockout/clamp control, and centering, the controls for that respective biopsy tool are also connected and made active.

A camera may also be attached to the active biopsy tool and advanced together with it. Alternately, the camera is inserted in advance of the biopsy tool, and is separately positioned from the biopsy tools.

It is noted that one or more tools may include an elastic, fluid-absorptive, textured surface to abrade a surface to expose and sample tissue, either alone or as part of another tool. According to one embodiment, the absorptive structure when dry is abrasive, and as it is hydrated, it becomes more pliant. The absorptive element may be impregnated with a salt or polymer, which is dissolved after brief exposure to intrauterine fluid.

In some cases, an electrical or electronic mechanism may be provided in the cartridge, for example to latch the mechanical controls, extend the sheath to a desire depth of insertion, rotate the brush, and retract the sheath and/or biopsy brush into the sheath. Typically, the extension of the biopsy brush and axial manipulation are user controlled, and not automated, though a completely automated biopsy is possible.

It is preferred that each biopsy tool have a mechanical limiter to control and constrain the movements within a predetermined range, wherein the predetermined range may differ for the various biopsy tools depending on their intended use of application. This helps avoid user error and resulting patient harm, and also helps reliably obtain usable specimens. Advantageously, axial control limits are referenced to the exterior surface surrounding the orifice of insertion, and the end of the barrel, a ring or protrusion surrounding the barrel, used to maintain this position reference without slipping into the orifice.

For example, the endocervical brush will typically have the sheath extend 0-2 cm past the orifice, and an endometrial brush will typically have the sheath extend 2-10 cm past the cervix, into the uterus, and a brush biopsy tool will extend 1-3 cm beyond the end of the sheath. The endocervical and endometrial brushes may be provided with or without suction, which may be provided by mechanical action of a plunger as the guidewire controlling the brush is withdrawn into the sheath, or by a vacuum provided through the sheath from the cartridge or beyond.

According to another embodiment, instead of a plunger, O-ring or piston within the sheath immediately proximal to the brush and distal to the cervical stop, it is also possible to generate a sampling vacuum at a more proximal region of the biopsy device, e.g., that is not inserted into the cervix, and has a larger diameter. This may be at or distal to the cervical stop. Thus, the volume drawn into the sheath by displacement of the guidewire at this wider cross section region will exceed the volume of the brush tip, permitting a larger volume sample, and/or higher vacuum force. A fluid, such as water, saline or silicone oil, may be may be provided in the sheath surrounding the guidewire, to permit hydraulic communication of the vacuum instead of pneumatic communication. The water, saline or oil may be confined to the device, and isolated from the biopsy sample and patient.

A puncher or cup biopsy tool are typically used under visual observation with the video imager, and may be less mechanically constrained in this circumstance, since the user is presumed to have control over the device during use.

Therefore, the present design permits multiple biopsies to be taken in a single session, from different regions of the organ, and maintained segregated from each other. From a patient perspective, this is advantageous, because the sampling procedure is facilitated, and the combined time and economic burden will typically be less than if separate biopsy tools are employed. Further, compatibility with a single imager used for a plurality of biopsy procedures is also efficient. Finally, in the case of a cartridge that disconnects from a standard handle, the cartridge provides an efficient way to organize and label (identify) the samples from a single patient, and makes pathological examination of the various samples from the same patient and same organ more efficient. Finally, because each sample is accurately depth labelled with respect to the orifice, clinically important information is obtained, as compared to traditional biopsy tools which do not provide an accurate depth reference. It is noted that a memory card, such as a micro-SD card, may be associated with the cartridge, which includes video and/or manipulation history information for each biopsy tool, which is automatically recorded and maintained, and which may be readily passed to the pathologist or made part of the patient's record. As discussed above, a non-contact electronic identification and/or information storage and/or secure authentication device may be employed, such as an ISO 14443 RFID device, to avoid contamination issues when using a contact device. Alternately, a barcode may be employed which allows reading of a record in a database or distributed database/blockchain.

It is an object to provide a flexible coaxial tissue sampling device, comprising: a sheath having a wall and a hollow space inside the wall; a displaceable wire within the hollow space, the displaceable wire having a first end extending from a proximal end of the sheath and second end configured, in a first state, to extend from a distal end of the sheath, and in a second state, to retract into the distal end of the sheath; the second end of the displaceable wire comprising a suction element, a cellular sampling structure, and a porous absorptive material, wherein the cellular sampling structure and the porous absorptive material are external to the sheath in the first state and internal to the sheath in the second state and the suction element is proximal to the cellular sampling structure and the porous absorptive material; the flexible coaxial structure being configured such that a tension on the first end of the displaceable wire at the proximal end of the sheath results in a retraction of the displaceable wire from the first state to the second state, to cause a displacement into the sheath of the displaceable wire and a corresponding proximal displacement of suction element, the cellular sampling structure, and the porous absorptive material, with suction of media external to the sheath into the distal end of the sheath, the porous absorptive material being configured to retain a fluid sample obtained in the first state after transition to the second state.

It is also an object to provide a flexible coaxial tissue sampling device, comprising: a sheath having a wall and a hollow space inside the wall; a displaceable wire within the hollow space, the displaceable wire having a first end extending from a proximal end of the sheath and second end configured, in a first state, to extend from a distal end of the sheath, and in a second state, to retract into the distal end of the sheath; the second end of the displaceable wire comprising a cellular sampling structure and a porous absorptive material, wherein the cellular sampling structure and the porous absorptive material are external to the sheath in the first state and internal to the sheath in the second state; the flexible coaxial structure being configured such that a tension on the first end of the displaceable wire at the proximal end of the sheath results in a retraction of the displaceable wire from the first state to the second state, to cause a displacement into the sheath of the displaceable wire, the cellular sampling structure, and the porous absorptive material, the porous absorptive material being configured to retain a fluid sample obtained in the first state after transition to the second state and to protect tissue from contact with the second end of the displaceable wire.

It is a further object to provide a biopsy method, comprising: providing a flexible coaxial structure comprising a sheath having a wall and a hollow space inside the wall; a displaceable wire within the hollow space, the displaceable wire having a first end extending from a proximal end of the sheath and second end configured, in a first state, to extend from a distal end of the sheath, and in a second state, to retract into the distal end of the sheath; the second end of the displaceable wire comprising a cellular sampling structure and a porous absorptive material, wherein the cellular sampling structure and the porous absorptive material are external to the sheath in the first state and internal to the sheath in the second state; inserting the distal end of the sheath through a cervix, past the internal cervical os, into a uterus, while the flexible coaxial structure is in the second state; pushing the first end of the displaceable wire into the sheath, to cause the flexible coaxial structure to assume the first state; manipulating the displaceable wire to obtain a cellular sample with the cellular sampling structure rubbing against the endometrium and the porous absorptive material absorbing fluid while protecting the endometrium from intrusion by a tip of the displaceable wire; applying a tension on the first end of the displaceable wire at the proximal end of the sheath to cause a retraction of the displaceable wire from the first state to the second state, and consequent withdrawal of the displaceable wire, the cellular sampling structure, and the porous absorptive material into the sheath, while retaining the absorbed fluid in the porous absorptive material; and capping the distal end of the sheath with the porous absorptive material to prevent contamination of a biopsy sample retained on the cellular sampling structure by cells within the cervix and vagina.

The cellular sampling structure may comprise a brush having a plurality of radially extending bristles from the displaceable wire and terminating in the porous absorptive material comprising an atraumatic bulb, covered by an open cell foam layer, further comprising a suction element displaceable with the displaceable wire and proximal to the cellular sampling structure and the porous absorptive material, configured to create a negative pressure within the sheath distal to the suction element when the displaceable wire is withdrawn into the sheath.

The porous absorptive material may cap the second end of the displaceable wire and protects tissue from damage by a tip of the displaceable wire. The porous absorptive material may be formed at a tip of the second end of the displaceable wire. The porous absorptive material in the second state and the sheath may together protect a biopsy sample within the sheath obtained during transition from the first state to the second state from contamination during withdrawal of the distal end from a patient. The porous absorptive material may be adapted for absorbing a biopsy sample for nucleic acid analysis. The porous absorptive material may be a sponge.

The cellular sampling structure may comprise a brush. The brush may comprise a plurality of bristles extending radially from the displaceable wire.

The coaxial structure may be configured to be inserted through an internal cervical os of a uterus of a human to retrieve an endometrial biopsy sample, having a depth adjustable during a biopsy procedure while the coaxial structure is maintained in the first state, by sliding of a depth stop on the sheath.

The coaxial structure may be configured to be inserted to a determined depth through an internal cervical os of a uterus of a human, to retrieve an endometrial biopsy sample, and to be withdrawn from the cervix. The coaxial structure may be further configured to be: inserted into the cervical os with the displaceable structure in the second state to a predetermined depth; extended into the first state with the cellular sampling structure within the uterus; manipulated by a user by movement of the first end of the displaceable structure to dislodge cells within the uterus; retracted into the second state within the uterus, to cause the vacuum to withdraw a liquid sample surrounding the cellular sampling structure in to the distal end of the sheath; and retracted from the cervical os with the displaceable structure in the second state.

The cellular sampling structure may comprise a spirally twisted steel wire with bristles extending therefrom, welded to a proximal guidewire.

The porous absorptive material formed at the second end may comprise a urethane foam provided over a cap terminating the spirally twisted steel wire.

The sheath ay have an outer diameter of about 0.15" and a length between 20 and 50 cm.

The tissue sampling device may further comprise a slidable skirt stopper provided on an exterior surface of the flexible sheath, configured to prevent insertion of the flexible sheath within the uterus of a patient beyond an axial location of the skirt stopper.

One embodiment provides at least two flexible coaxial structures, each having a respective sheath, a respective displaceable wire, a respective suction element, a respective cellular sampling structure and a respective porous absorbent material; and a housing, configured to selectively engage and disengage a respective displaceable wire of a respective flexible structure to a user interface, such that when engaged, tension and compression are passed from the user interface to the displaceable structure to transition the displaceable structure between the first state and the second state, and when disengaged, tension and compression are not passed from the user interface to the displaceable structure.

The tissue sampling device may further comprise an electrical motor configured to move the displaceable structure, e.g., axially and rotationally.

It is therefore an object to provide a tissue sampling device, comprising: a flexible sheath having at least a distal portion configured to maintain an internal vacuum; a displaceable structure within the sheath, to form a coaxial structure; the displaceable structure having a first end extending from a proximal end of the sheath and second end configured to, in a first state, extend from a distal end of the sheath, and in a second state, to be retracted into the distal end of the sheath; the second end of the displaceable structure having a cellular sampling structure, preceded by a proximal suction element and having a distal porous absorptive material formed at the distal tip; and the coaxial structure being configured such that a tension on the first end of the displaceable structure at the proximal end of the sheath results in a retraction of the displaceable structure from the first state to the second state, to generate the suction to cause a displacement of media external to the sheath into the sheath distal to the piston.

The tissue sampling device may further comprise an element displaceable with the displaceable structure, configured to create a negative pressure within the tubular sheath distal to the element when the displaceable wire is withdrawn into the tubular sheath.

The cellular sampling structure may comprise a brush.

The brush may comprise a plurality of bristles extending radially from the displaceable structure. The brush may have a helical cross-section profile.

The coaxial structure may be configured for insertion to a predetermined depth into a cervical os of a uterus of a human, to retrieve an endometrial biopsy sample, and to be withdrawn from the cervical os of the uterus.

The coaxial structure may be further configured to be: inserted into the cervical os with the displaceable structure in the second state to a predetermined depth; extended into the first state with the cellular sampling structure within the uterus; manipulated by a user by movement of the first end of the displaceable structure to dislodge cells within the uterus; retracted into the second state within the uterus, to cause the vacuum to withdraw a liquid sample surrounding the cellular sampling structure in to the distal end of the sheath; and retracted from the cervical os with the displaceable structure in the second state.

The cellular sampling structure may comprise spirally twisted steel wire with bristles extending therefrom, welded to a proximal guidewire. The distal porous absorptive material formed at the distal tip may comprise a urethane foam provided over a cap terminating the spirally twisted steel wire.

The sheath may have an outer diameter of about 0.15" and a length between 20 and 50 cm.

The tissue sampling device may further comprise a skirt stopper provided on an exterior surface of the flexible sheath, configure to prevent insertion of the flexible sheath within the uterus of a patient beyond an axial location of the skirt stopper. The skirt stopper may comprise a flanged element on an outer surface of the flexible sheath, and the flexible sheath is configured for insertion into the cervical os of a uterus of a human to the predetermined depth, to retrieve an endometrial biopsy sample from inside the uterus, and to be withdrawn from the cervical os of the uterus after the endometrial biopsy sample is obtained, further configured to be: inserted into the cervical os with the displaceable wire in the second state to the predetermined depth; extended into the first state with the cellular sampling device within the uterus; manipulated by movement of the first end of the displaceable wire to dislodge endometrial cells; retracted into the second state within the uterus, to draw the vacuum to withdraw a liquid sample surrounding the cellular sampling device in to the distal end of the tubular sheath; and retracted from the cervical os with the displaceable wire in the second state.

The tissue sampling device may further comprise a plurality of flexible sheaths, each having at least a distal portion configured to maintain an internal vacuum; a respective of displaceable structure within each flexible sheath, to form a set of coaxial structures; and a housing, configured to selectively attach a respective displaceable structure to a user interface, such that when engaged, tension and compression are passed from the user interface to the displaceable structure to transition the displaceable structure between the first state and the second state, and when disengaged, tension and compression are not passed from the user interface to the displaceable structure.

The tissue sampling device may further comprise an electrical motor configured to displace the displaceable structure. The tissue sampling device may further comprise an electrical motor configured to rotate the cellular sampling structure.

It is also an object to provide a multiple-sample biopsy device, comprising: a plurality of flexible sheaths; a displaceable structure within each sheath, to form a coaxial structure; each displaceable structure having a first end extending from a proximal end of the sheath and second end configured to, in a first state, extend from a distal end of the sheath, and in a second state, to be retracted into the distal end of the sheath; the second end of the displaceable structure having a cellular sampling structure distally terminated in a porous absorptive foam; and a housing, configured to selectively attach a respective displaceable structure to a user interface, such that when engaged, tension and compression are passed from the user interface to the displaceable structure to transition the displaceable structure between the first state and the second state, and when disengaged, tension and compression are not passed from the user interface to the displaceable structure.

It is also an object to provide a tissue sampling method, comprising: providing a coaxial structure, comprising a flexible sheath having at least a distal portion configured to maintain an internal vacuum, and a displaceable structure within the sheath, to form a coaxial structure, the displaceable structure having a first end extending from a proximal end of the sheath and second end configured to, in a first state, extend from a distal end of the sheath, and in a second state, to be retracted into the distal end of the sheath, and the second end of the displaceable structure having a cellular sampling structure, preceded by a piston and terminated by a porous absorptive tissue-abrasive structure; and applying a tension on the first end of the displaceable structure at the proximal end of the sheath to case retraction of the displaceable structure from the first state to the second state, generating the vacuum.

The coaxial structure further may comprise a skirt around the flexible sheath, configured to limit an insertion depth of the flexible sheath into a human cervix.

The coaxial structure may be configured for insertion into the cervical os of uterus of a human to the predetermined insertion depth defined by an axial position of the skirt around the flexible sheath, to retrieve an endometrial biopsy sample, and to be withdrawn from the cervical os of the uterus.

The method may further comprise: inserting the distal portion of the coaxial structure into the cervical os of a uterus, with the displaceable structure in the second state to the predetermined depth; extending the distal portion of the coaxial structure into the first state with the cellular sampling structure within the uterus; manipulating the first end of the displaceable structure to dislodge cells within the uterus; retracting the coaxial structure into the second state within the uterus, to cause the vacuum to withdraw a liquid sample surrounding the cellular sampling structure in to the distal end of the sheath; and retracting the distal portion of the coaxial structure from the cervical os with the displaceable structure in the second state.

The cellular sampling structure may comprise a brush having a plurality of radially extending bristles from the displaceable structure and terminating in an atraumatic bulb, covered by an open cell foam layer.

The cellular sampling structure may comprise a spirally twisted flexible wire with bristles extending therefrom, may further comprise twisting the guidewire to thereby rotate the cellular sampling structure.

It is another object to provide a flexible coaxial biopsy device, comprising: a tubular sheath having a wall configured to maintain an internal vacuum with respect to an exterior of the tubular sheath; a displaceable wire within the tubular sheath; and a cellular sampling device distally terminated with a porous absorptive structure, each of the cellular sampling device and the porous absorptive structure being configured to disrupt a surface of a tissue, mounted on the displaceable structure distal to the element, configured to protrude from a distal end of the tubular sheath when the displaceable element is disposed in a first state, and to be contained within the distal end of the tubular sheath when the displaceable element is disposed in a second state.

The flexible coaxial biopsy device may further comprise a flanged element on an outer surface of the tubular sheath, configured to limit a depth of insertion of the tubular sheath into a cervix.

The cellular sampling device may comprise a plurality of bristles extending outwards from the displaceable wire, terminating at the distal end in an atraumatic bulb covered by the porous absorptive structure comprising a foam layer.

The flexible coaxial biopsy device may be configured for insertion into the cervical os of a uterus of a human to the predetermined depth, to retrieve an endometrial biopsy sample from inside the uterus, and to be withdrawn from the cervical os of the uterus after the endometrial biopsy sample is obtained.

The flexible coaxial biopsy device may further comprise an element that creates a negative pressure within the tubular sheath when the displaceable wire is withdrawn into the tubular sheath.

The biopsy brush described above may also be revised for use as an anal biopsy brush, and an endometrial biopsy brush and anal biopsy brush may be provided together as a kit, optionally alone with a vial of preservative solution (for a single brush), or a plurality of vials of preservative for a kit. The kit is preferably a sterile package, which may be double wrapped, containing the biopsy brush or bushes, a vial or vials of preservative, and optionally an acceptable lubricant for cytological sampling, and optionally a disposable sterile sheet or drape.

The anal biopsy brush differs from an intrauterine biopsy brush in that it will be shorter, since the working distance between the physician or caregiver and patient orifice is less. The, for intrauterine use, the sheath is typically 20-25 cm long, with a 4 cm long brush and 2 cm exposed guidewire, such that the wire is 26-31 cm long, past the end of the handle to which it is bound, with a skirt on the sheath about 4 cm from the distal end.

An anal biopsy brush sheath will typically be 8-12 cm long, with the skirt about 4 cm from the distal end. For example, an anal biopsy brush may have a sheath 8 cm long with the skirt located 4 cm from the distal end, having a guidewire 14-18 cm long for sampling in the rectum up to 6 cm past the end of the sheath. The absorptive tip is preferably provided.

A kit may therefore include a long intrauterine biopsy device having a sheath length of about 20 cm, a short anal biopsy device having a sheath length of about 8 cm, two vials of cytological preservative, a packet of water-based cytologically acceptable lubricant (e.g., Surgilube®, which preferably does not include carbomers), a sterile drape, and package insert labelling instructions (which may be imprinted on the packaging as appropriate). Any lubricant should be applied on the exterior of the sheath, between the skirt or flange and distal tip, with the brush in the retracted position, with care taken to avoid getting lubricant on the end of the sheath or brush.

DETAILED DESCRIPTION OF THE PREFERRED EMBODIMENTS

Example 1

Figure 8A:
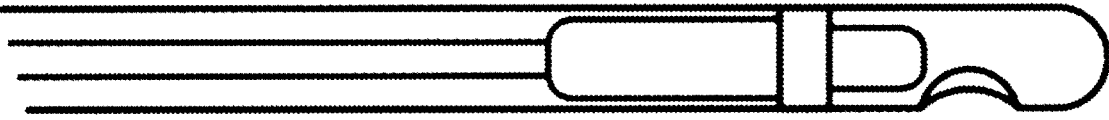
FIGS. 8A and 8B show a Pipelle endometrial biopsy device of the prior art, in the extended and retracted states, respectively.
Figure 8B:
Figure 11:
FIG. 11 shows a guidewire and biopsy brush according to the present invention with a sponge covering an atraumatic bulb.
Figure 12:
FIG. 12 shows a narrow sheath with skirt stopper installed according to the present invention.
Figure 13:
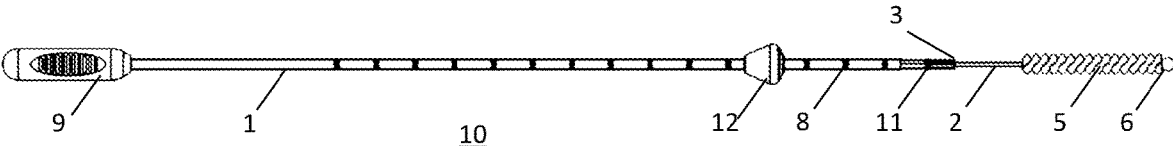
FIG. 13 shows a complete biopsy device with manually operable handle, skirt stopper, sheath, guidewire, brush, O-ring, and a sponge covering an atraumatic bulb according to the present invention.

A preferred embodiment of the present invention is shown in FIGS. 12 and 13, and consists of an intrauterine biopsy device 10 having an outer thin walled sheath 1 of approximately 2.25 mm outside diameter and 1.2 mm inside diameter; length is between 20-50 cm, e.g., 22 cm. This sheath 1 may be a clear, bendable but self-supporting plastic tube, made e.g., of nylon. The guidewire 2 is preferably a twisted stainless steel wire of approximately 0.1-0.2 mm diameter, having sufficient mechanical properties to convey the forces for extension and retraction of the biopsy brush 5 during use. At the distal end of the guidewire 2 is a biopsy brush 5, shown in FIGS. 8 and 11, tipped with an atraumatic bulb 6. The biopsy brush 5 may be about 4 cm long, and extend about 2 cm past the end 3 of the sheath 1 when extended. An O-ring 11 preferably remains within the sheath 1 over the entire range of travel, to avoid problems re-engaging the end 3 of the sheath 1. For example, the O-ring 11 (or more generally, plunger attached to the guidewire 2) may be, for example, 2-5 mm from the end of the sheath 1 when extended.

An anal biopsy device may also be provided, having an outer thin walled sheath 1 of approximately 2.25 mm outside diameter and 1.2 mm inside diameter; length is between 8-12, e.g., 8 cm. This sheath 1 may be a clear, bendable but self-supporting plastic tube, made e.g., of nylon. The guidewire 2 is preferably a twisted stainless steel wire of approximately 0.1-0.2 mm diameter, having sufficient mechanical properties to convey the forces for extension and retraction of the brush during use. At the distal end of the guidewire 2 is a biopsy brush 5, shown in FIGS. 8 and 11, tipped with an atraumatic bulb 6. The biopsy brush 5 for the anal biopsy device may also be 4 cm long, with the O-ring 11 or plunger 2-5 mm the end of the sheath 1 when the biopsy brush 5 is extended.

The guidewire 1 may be periodically marked 8, such as in 1 cm increments, so that the physician or biopsy device operator can estimate the biopsy brush 5 insertion with respect to the proximal end 3 of the sheath 1.

Figure 10A:
Figure 10B:
Figure 10C:

At one end, the one that enters the uterus or anus, the biopsy brush 5 is formed. A tight-fitting O-ring 11 around the guidewire 1, similar to that shown in FIGS. 10A-10C, acts as a piston and creates the suction as the O-ring 11 is withdrawn through the outer thin walled sheath 1.

In another embodiment, the O-ring 11 may be disposed about 2.5 cm from the tip, with the biopsy brush 5 extending about 1.5 cm from the tip, with 1 cm of bare wire of the guidewire 2 between them.

Figure 9:
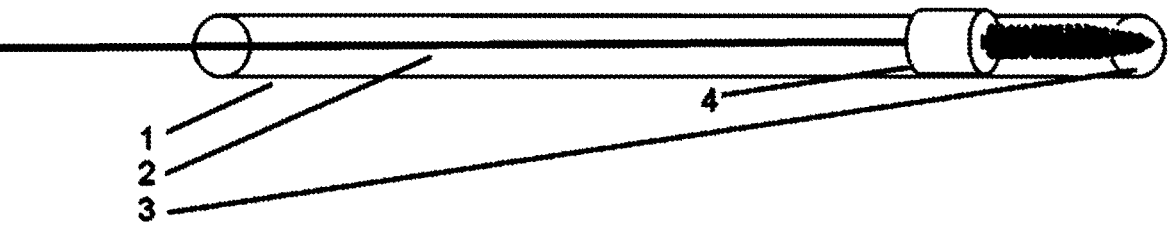
FIGS. 9 and 10A-10C show a prior art endometrial biopsy brush with suction, according to U.S. Pat. Nos. 9,351,712, 8,920,336, 8,517,956, and 8,348,856.

As shown in FIGS. 9, 10 and 11, a skirt stopper 12 is provided about the exterior of the thin walled sheath 1, near the distal end, which may be in fixed position or manually slidable. The skirt stopper 12 is approximately 1 cm in diameter, and may be formed of nylon, polyurethane, silicone, neoprene, or other medically acceptable plastic or rubber. Typically, the skirt stopper 12 is fixed in position, and may be glued (e.g., UV activated methyl-methacrylate adhesive) or molded to the sheath 1 in position.

The biopsy device is use as follows:

The biopsy brush 5 is retracted completely into the outer sheath 1.

The sheath 1 is inserted, through the vagina, into the cervix, until the skirt stopper 12 meets the external os of the cervix. The tip of the biopsy brush 5 should be displaced from the fundus.

The outer sheath 1 is pulled back until it stops, i.e., abuts the handle 9. The biopsy brush 5 is then rotated by holding the sheath 1 still and turning the handle 9. For example, the biopsy brush 5 may be rotated in a clockwise manner until a reference mark on the handle 9 indicates completion of a 360° turn, and then rotated counterclockwise until the reference mark on the handle 9 indicates completion of a −360° turn. Alternately, the biopsy brush 5 may be rotated in only one direction by completing 4 or 5 360° rotations. In some cases, the biopsy brush 5 may be repositioned axially, though it should not be withdrawn into the sheath 1 until the sampling is completed.

After sampling with the biopsy brush 5, the guidewire 1 is pulled at the handle 9, until the sheath 1 hits the stop (e.g., the edge of the handle), thereby suctioning fluid surrounding the tip into the sheath 1, and then withdrawing the biopsy brush 5 into the sheath 1.

After withdrawal of the device 10 from the vagina, the biopsy brush 5 and fluids in the sheath 1 are immersed in a cytology preservative, such as formalin, and the sample is washed from the biopsy brush 5 into the preservative by moving the biopsy brush 5 in and out of the sheath 1 immersed in the fluid.

The invention may be used, for example, to sample the inside of the uterus to diagnose abnormalities. It can detect or exclude a cancer. It can obtain an adequate tissue sample to determine infertility causes.

The anal brush biopsy tool is similarly employed. Such a biopsy tool typically has a shorter sheath 1 and guidewire 2 than an endocervical brush biopsy tool, because of the easier anatomical access. For example, the sheath 1 may be 10-15 cm long, and the biopsy brush 5 may extend 2-6 cm beyond the end of the sheath 1. As with the endocervical brush biopsy tool described above, a skirt stopper 12 is preferably provided which prevents insertion of the sheath 1 into the anus beyond the sheath 1, to provide a physical reference distance for insertion. In some cases, the skirt stopper 12 may be repositioned on the sheath 1, to permit the physician the ability to determine at what depth of insertion the sample should be acquired. Advantageously, the readjustment requires more force than would be available by applying an unconstrained compression of the sheath 1 against the skirt stopper 12, so that the position is maintained during use, but the stiction force can be overcome when the biopsy tool 10 is external to the body.

A rough absorptive tip may be provided to abrade the uterine surface and absorb a liquid sample during the biopsy.

Example 2

Figures 14, 15, 16, 17, 18, 19:
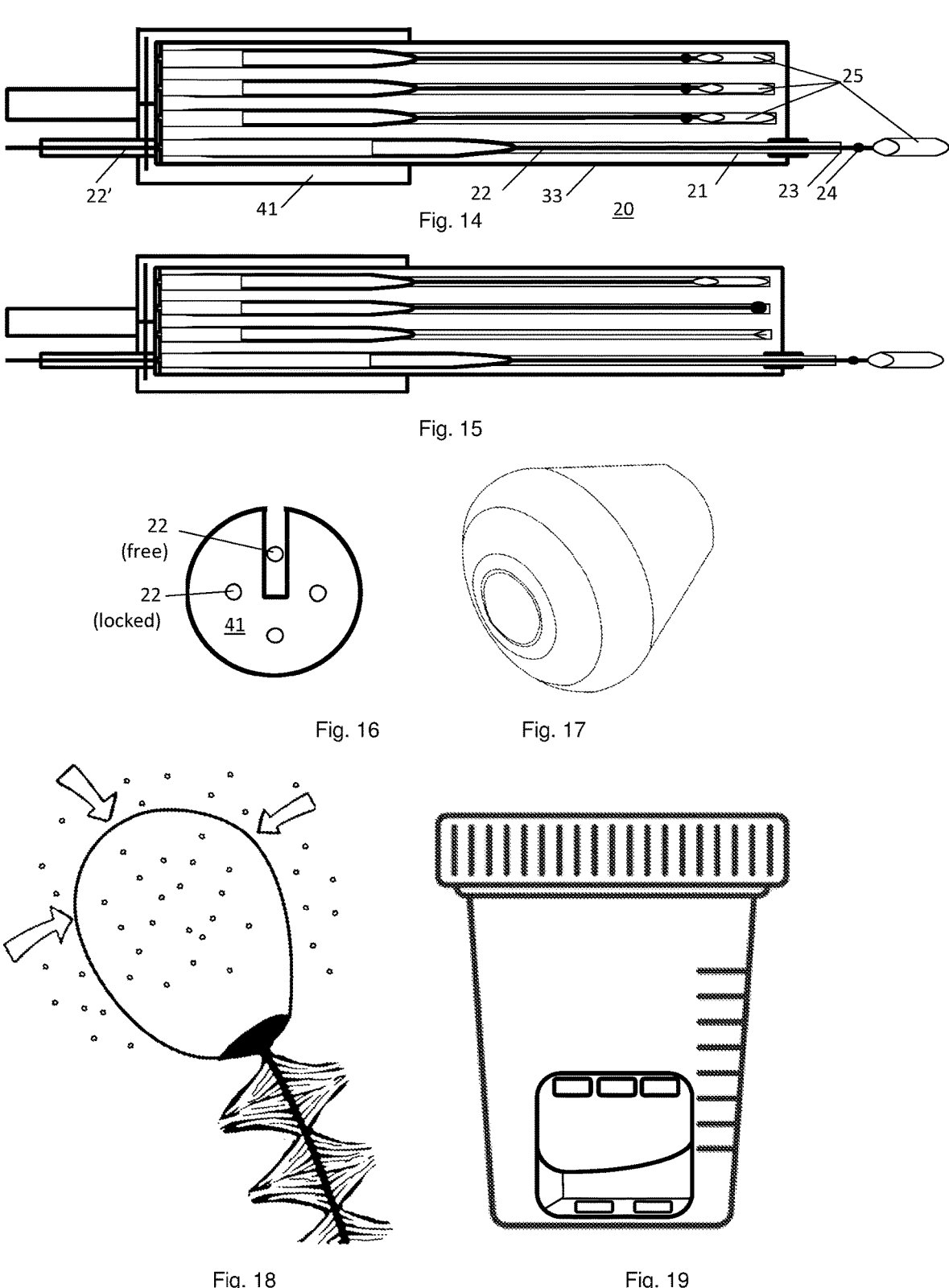
FIG. 14 shows an arrangement of an independently controllable, biopsy multiple sample, biopsy device showing four similar biopsy sampling tools.
FIG. 15 shows an arrangement of an independently controllable, biopsy multiple sample, biopsy device showing four different biopsy sampling tools.
FIG. 16 shows a detail of a selector which permits manipulation of a single biopsy sampling tool in a barrel cartridge.
FIG. 17 shows a shirt stopper according to the present invention.
FIG. 18 shows a side perspective view of a prototype biopsy device, having an absorptive sponge material at the distal tip of the biopsy device, with a schematic representation of absorption of a sample.
FIG. 19 shows a specimen collection container, with a pocket to retain the biopsy brush.
Figure 20A:
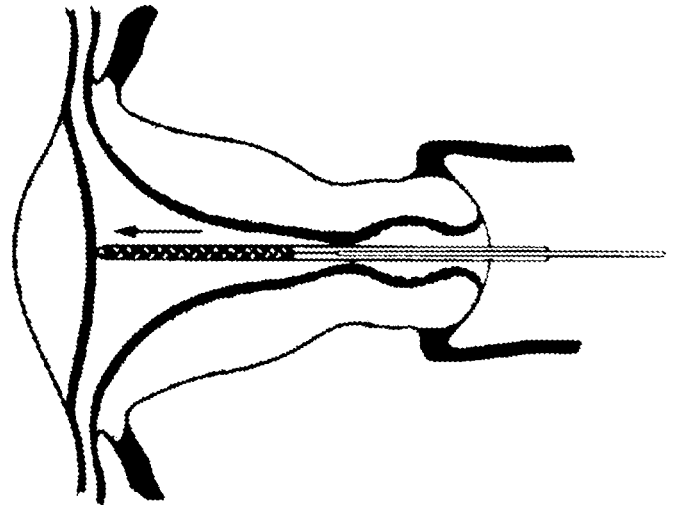
FIG. 20A shows insertion of a prior art biopsy tool into the uterus.
Figure 20B:
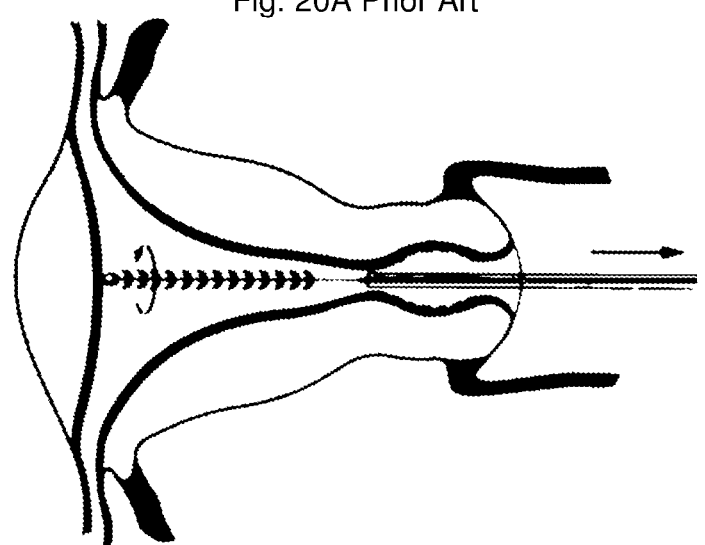
FIG. 20B shows manipulation of a prior art biopsy tool into the uterus for tissue sampling.
Figure 20C:
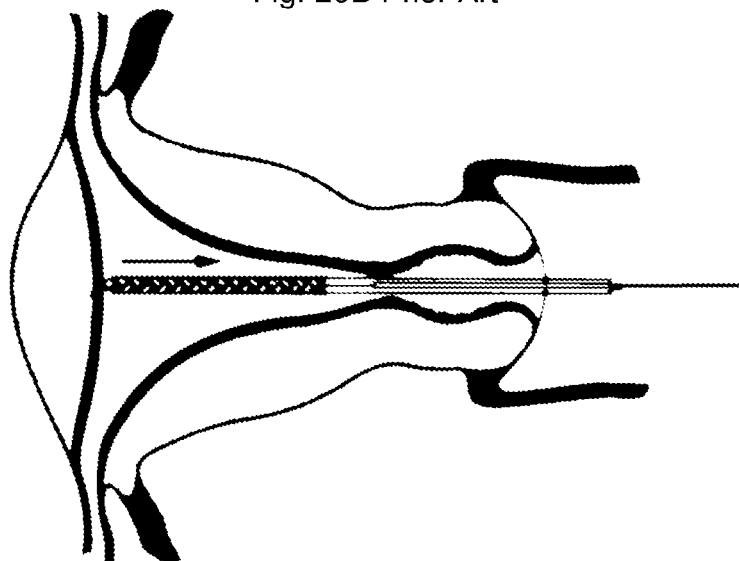
FIG. 20C shows withdrawal of a prior art sampling brush into a sheath for subsequent removal from the uterus.

According to a second embodiment as shown in FIGS. 14-16, a multiple sample biopsy device 20 is provided, capable of obtaining and segregating a plurality of biopsy samples taken in a single session. This therefore requires a plurality of biopsy brushes 25 or tools, and a plurality of sheaths 21 in which the tools are extended and retracted.

As discussed above, a depth of insertion positional reference, such as a skirt stopper 32 may be provided. However, where the multiple biopsy tool 20 system has a mechanism maintained outside of the orifice, the diameter of the tool may be sufficiently large to act as the stopper without additional structures.

According to one design, each biopsy tool is separate, including a sheath 21 and guidewire 22 control. A set of biopsy tools are aggregated in an outer tube housing 33. The outer tube housing 33 has a conical internal profile at the distal end, so that a single biopsy tool may be advanced past the end of the housing, into the orifice or canal from which a biopsy is to be taken. In some cases, endoscopic guidance of the biopsy is desired, and in that case, a second sheath which supports the endoscope and lighting may be advanced as well. The endoscope sheath may also inject saline for visualization, though in the case of a brush biopsy, this is disfavored, since the saline will wash away the dislodged cells, and reduce the positional accuracy of sampling. An inert gas, such as $CO_2$ may also be injected through the sheath, in known manner.

One or more tools may have a rough absorptive tip may be provided to abrade the uterine surface and absorb a liquid sample during the biopsy.

For example, the multiple biopsy tool 20 may be provided in a 3 mm tube sheath 21, with 6 separate brushes 25 provided within a housing. A stop may be provided at the proximal end of each sheath within the housing, to prevent over-withdrawal. Markings may be provided on each sheath 21, to inform the physician about the depth of insertion. In some cases, the physician may intend gradated sampling at a series of depths in the orifice, and advantageously, each respective sheath may have a stopper which limits its depth of insertion, and provides the physician with haptic feedback when that depth is achieved. This stopper may be a simple O-ring or clamp, which is adjusted by the physician for each biopsy sampling tool, before the procedure. The guidewire 21 for each sampling tool may also have depth limits. Of course, the retracted position with the biopsy tool fully withdrawn into the sheath 21 represents one extreme, and a clamp or limit may be provided on the manipulation end to control how far the guidewire 22 may be extended beyond the end of the sheath 21.

In this first design, each biopsy brush 25 may be of known type, with the optional addition of the insertion and retraction limiters, and an optional absorptive tip, and indeed, the housing for arranging a multiple biopsy sample session may itself may be provided independent of the biopsy brushes 25.

Note that the absorptive structure need not be at the extreme tip, and in fact may be displaced in some cases.

In general, the larger housing diameter avoids the need for a separate skirt stopper, though the housing may terminate in a skirt stopper.

Example 3

According to a second design of the multiple sample biopsy device, a single manipulator extends from a housing, which itself contains a plurality of biopsy tools.

As discussed above, a depth of insertion positional reference, such as a skirt stopper may be provided. However, where the multiple biopsy tool system has a mechanism maintained outside of the orifice, the diameter of the tool may be sufficiently large to act as the stop without additional structures.

Thus, a selectively engageable coupling is provided between a single guidewire and the various tools. The coupling thus links the guidewire, that extends to a physician manipulation interface, such as a grasping element, a handle, or a pivotal mechanism, to the individual guidewire for each tool. Advantageously, the plurality of tools are provide in a rotating barrel 41, which serves as the housing. Each biopsy tool, when engaged with the manipulation guidewire 21, can be advanced with its respective sheath 22 an insertion distance, and then the biopsy brush 25 advanced beyond the sheath 21, and twisted or otherwise manipulated to obtain a biopsy sample. The biopsy brush 25 is then withdrawn back into the sheath 21, the sheath 21 with biopsy brush 25 covered then withdrawn back into the cartridge, and the rotating barrel 41 twisted so another biopsy tool may then be engaged.

Therefore, the coupling is a coaxial coupling, which separately links and controls the sheath 21 and the guidewire 22 within each respective sheath 21. For example, within the cartridge, the end of the sheath 23 may terminate in a steel ring, which is magnetically permeable. Thus, a magnetic coupling can be used to connect and disconnect the sheaths 21. Further, the inactive biopsy tools may also be held in place by another magnet, which is typically an electromagnet, or a permanent magnet with an electromagnetic release. The guidewire 22 may be selectively connected to the external manipulation guidewire 22' with a spring-loaded clamp. As the rotating barrel 41 is turned, the spring-loaded clamp releases, and re-engages as it reaches the next detent position with the next biopsy tool aligned with the spring clamp. Within the rotating barrel 41, the guidewire 21 from the biopsy tool extends beyond the proximal end of the respective sheath 22.

The rotating barrel 41 is typically at least as long as the desired depth of insertion of the sheath 21 into the patient. Thus, if it is desired to have a 12 cm depth of insertion, the rotating barrel 41 mechanism may be 13-16 cm long.

As shown in FIG. 14, a plurality of similar brushes 25 are provided in a cartridge. In FIG. 15 a plurality of different brushes are provided in the cartridge. The cartridge has an exit port for the engaged biopsy tool. Each brush has its own associated sheath, which may be independently advanced into the patient, depending on which tool is engaged. A mechanism at the proximal end of the housing controls the selection of the barrel position by an angle of rotation, the latching of the sheath of the respective active tool to the tool advancement control, the clamping of the guidewire of the respective active tool to the guidewire control for manipulation by the physician, and in some cases, other controls, such as deflection angle of the sheath.

FIG. 16 shows an end view of a portion of the mechanism in the rotating barrel 41, wherein one guidewire 22 is free to be manipulated by the physician, while access for manipulation of the other guidewires 22 is locked out.

FIG. 14 shows a bulb 24 provided just proximal to each sampling brush 25, which is provided to draw a sampling vacuum when the respective brush 25 is withdrawn back into the sheath 21.

In FIG. 15, not all biopsy tools have such a feature. The biopsy sampling tools, may be, for example, an endocervical sampler, an endometrial sampler, a punch sampler, and an endometrial sampler with suction.

In some cases, the sheath 21 itself may be articulable or angularly guidable to direct the biopsy tool to a desired region. The articulable sheath 21 may be a single axis, i.e., a curvature of the end 23 of the sheath 21, typically as a result of a tension on a tensile element such as cable, guidewire 22 or filament attached to the wall of the sheath 21, not shown in in the figures. By controlling the angle of curvature, and the rotational angle of the sheath 21 with respect to the organ, a reasonable range of control is provided. Similarly, a punch, or snare, or encapsulating biopsy device may also be controlled by a tension, which may be a wire or polymer filament. Thus, the case of a single guidewire 21 with a single degree of freedom (advance/retract) is a simplest case, and additional controls and degrees of freedom may be provided. Note that an shape memory alloy (SMA) actuator may also be used to alter the tension. The controls for these tools may also be selectively engaged through a mechanism, or provided individually to the user.

An endoscopic imager (not shown in the figures) may be provided, preferably as a feature of the housing, so that it may be used with various biopsy tools within the housing. For example, a 1-3 mm endoscopic camera with fiber optic or direct LED lighting, may be provided, e.g., the On Semiconductor OVM6946 ¹⁄₁₈" 400×400 imager.

Example 4

FIG. 18 shows a side perspective view of a prototype biopsy device, having an absorptive sponge material at the distal tip of the biopsy device. A longer foam tip allows for more fluid absorption but requires that the brush is shorter for the same length device. The foam may have a length of 0.25". The absorptive foam tip is placed over an acrylic ball at the end of the guidewire, which is free from bristles for the length of the foam. The foam may be attached to the brush by using FEP heat shrink to compress the proximal end of the foam, and applying UV glue (Loctite 4011 or 4306 or AA 3979) prior to removing the heat shrink.

The sheath has an OD of 0.150". When retracted, the maximum fluid sample drawn by the vacuum was 0.51 ml. The volume absorbed by the foam tip was 0.03-0.05 ml for water and 0.62-0.72 for 5000 cSt fluid.

The brush may be straight natural 6-12 Nylon filament, on a 304SS core, terminated in an acrylic ball. The twisted wire for the brush is welded to the core wire proximate to the brush.

The dimensions of a preferred embodiment are as follows:
Brush Diameter: 0.118"±0.010", Brush Length: 1.25"±0.125"
Overall Length: 12"±0.125", Distance from Tip to Bristles: 0.25"
Core Wire 304SS spring tempered, Diameter: 0.018"
Twisted Wire 304SS Diameter 0.037"
Bristles Straight Natural 6-12 Nylon Filament 0.003" Single Stem/Single Spiral, angled at 45 degrees from the core wire
Acrylic Ball on Tip: 0.055"±0.015" Diameter
The handle is, e.g., textured and ergonomically shaped with a concave profile, Tecoflex 60D with 20% BaSO₄, about 1.5" long and 0.313" diameter.
The skirt is polycarbonate (Calibre 2061) or silicone, 0.787" diameter, 0.742" long, with a biconic intersection profile with angles of 30° and 60°, and smoothed edges.
Nusil Med-360 silicone fluid, 1000 cP, may be used to lubricate the sheath, and seal the vacuum draw mechanism. The plunger for drawing vacuum is 0.118" long, 0.135" diameter formed of NuSil-4970 silicone, and has sealing surfaces at each end with a central recess. The plunger is compression fit around the wire, proximal to the brush.
The foam tip is, for example, a urethane foam, which in a prototype was obtained from a Puritan 1135 Purswab® foam-tipped applicator (Puritan Medical Products Co., Guilford, ME), though in practice, will be custom made.

The device is designed to maximize cell collection during the biopsy process in doctor's office. It combines global endometrial disruption using a brush, with a built-in suction process and absorption, created by a sponge. A series of tests allowed selection of an optimal brush. It has a smaller diameter, compared to its competitors (0.118"±0.010" and length of 1.25"±0.125") promoting a reduction in discomfort during the procedure, while providing a satisfactory tissue sampling.

After tissue disruption is completed, the sponge tip absorbs additional fluid and material and the device creates a vacuum that aspirates further tissue sample into the device sheath. The idea of aspiration differs from suction used in other devices. The suction will not directly obtain the tissue from the uterine wall, and rather it will aspirate the tissue that was previously scraped off the uterine wall by the brush assuring a better patient experience. The sponge tip prevents the puncture of the uterine wall and due to absorption provides additional tissue collection and fluid intake. A guard (e.g., formed of polycarbonate) rests on the cervix during the procedure and prevents over-insertion of the device.

Figures 1, 2, 3, 4, 5, 6:
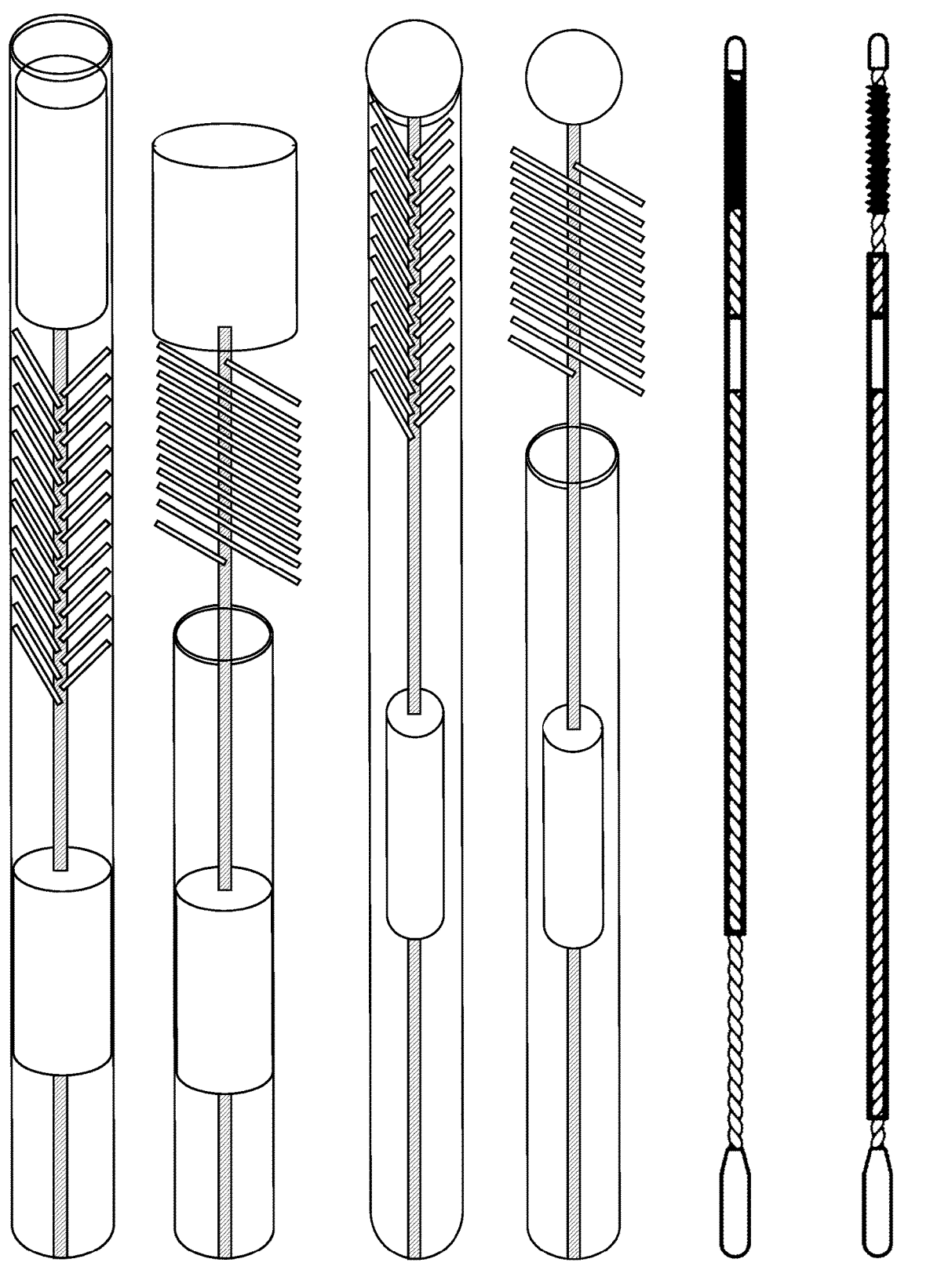
FIGS. 1 and 2 show a first embodiment of the biopsy device according to the present invention with a cylindrical sponge cap in the retracted and extended state.
FIGS. 3 and 4 show a prior art Tao Brush in the retracted and extended state with respect to the sheath, respectively.
FIGS. 5 and 6 show a second embodiment of the biopsy device according to the present invention with a round cap, in the retracted and extended state.
Figure 7:
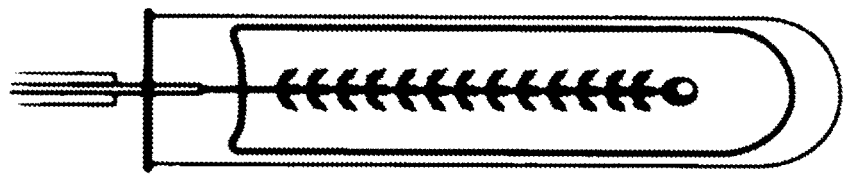
FIG. 7 shows transfer of the biopsy sample to a tube containing brush cytology preservative.
Figures 21A, 21B, 21C:
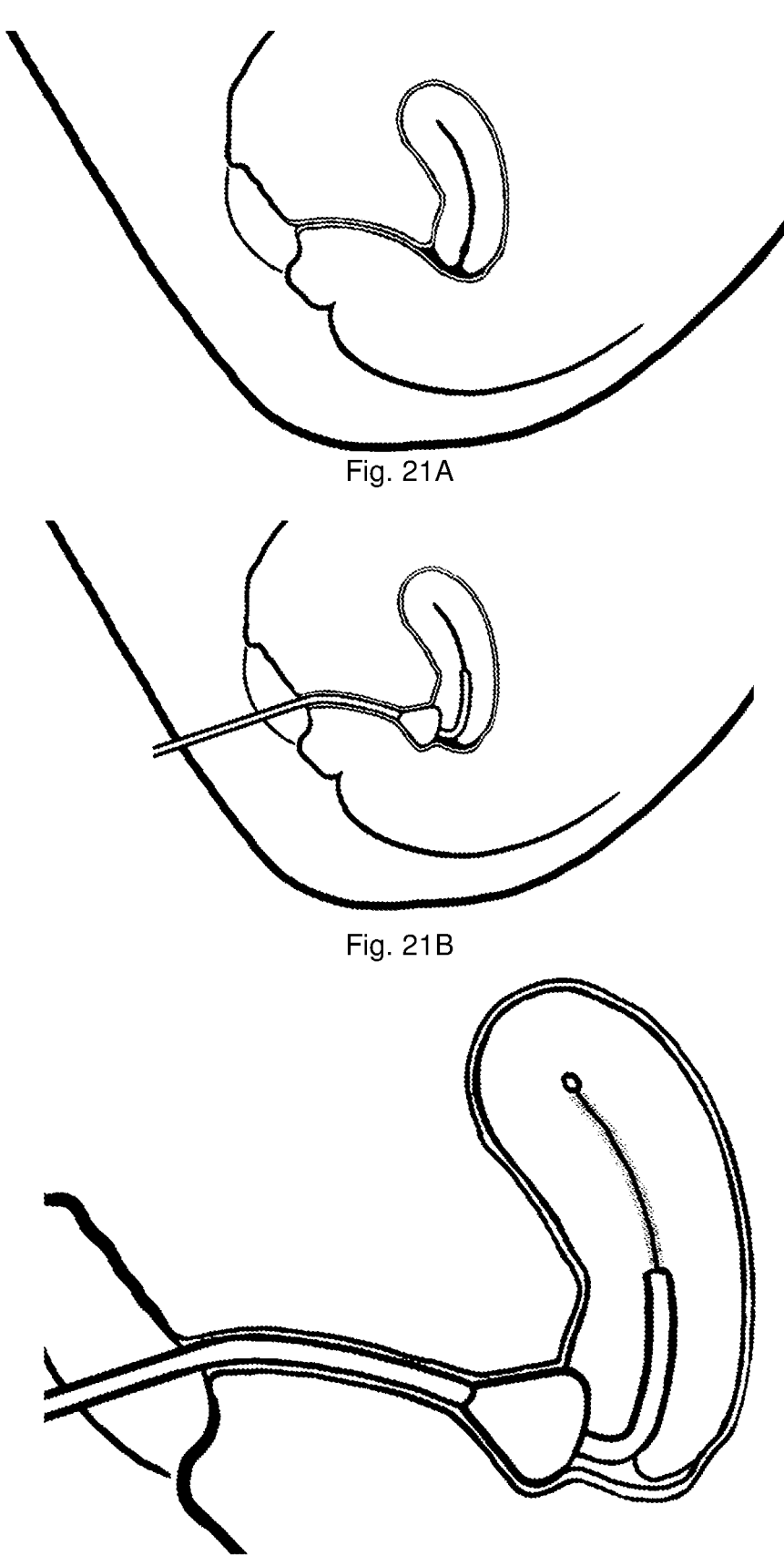
FIG. 21A shows a side view of vaginal canal/uterus in cross section.
FIG. 21B shows that the device according to the present invention travels into the vaginal canal, enters cervix, and stops when the skirt touches the cervix with the brush encased within the sheath inside the uterus.
FIG. 21C shows the brush extending in full length of the inside the cavity of the uterus, with an absorptive sponge covering an atraumatic bulb and the distal tip.

The procedure proceeds as follows:

1. Procedure: Place the patient in lithotomy position, generally shown in FIG. 21A. Gently insert the speculum and open to expose the uterine cervix. FIG. 21A shows a side view of vaginal canal/uterus in cross section. Only the labia, vagina, cervix, and uterus are depicted, as well as an outline of the patient's skin. The position of the pelvis and legs will suggest the patient is in the examination position.
2. Assure that the brush is completely retracted into the outer sheath.
3. Gently insert the outer sheath of the device though the cervix into the uterus and stop when the skirt (guard) touches the cervix. (FIG. 21B)
4. Extend the brush by gentle push of the handle until resistance of the tip is upon meeting the fundus of the uterus. (FIG. 21C)
5. Rotate the sampler in a clockwise manner and complete up four or five 3600 rotations.
6. The sponge on the tip protects the fundus from piercing. It creates additional tissue sampling by absorption of the fluid and the cells from the uterus.
7. Pull the handle back. The suction created by the plunger located inside of the sheath provides aspiration of the cells and prevents loss of the sample from the brush.
8. Immediately immerse the sample into the preservative solution, see FIG. 7 or FIG. 19.
9. Handle the sample and brush as directed by the pathology lab.

FIG. 18 shows a detail of a tip of the biopsy brush, wherein a sponge sits at the tip of the device, distal to the brush, and provides cushioning of the tip as well as a volume for sampling of cell-containing fluid from the endometrium.

FIG. 19 shows a specimen collection container, with a pocket to retain the biopsy brush, e.g., after it is cut or severed from the full biopsy device. The specimen collection container may have an RFID, bar code, or 2D bar code (or QR code) for identification. In some cases, the RFID is transferred from the full biopsy device to the specimen collection container with the biopsy brush portion thereof. The pocket may be tamper-evident, and thus provide increased security and authentication through the chain of transport.

What is claimed is:

1. A flexible coaxial tissue sampling device, comprising:
   a sheath;
   a displaceable wire within the sheath, the displaceable wire having a first end extending from a proximal end of the sheath and second end configured, in a first state, to extend from a distal end of the sheath, and in a second state, to retract into the distal end of the sheath;
   an atraumatic bulb covered with a porous absorptive material comprising a polymeric foam, formed on the second end of the displaceable wire, the atraumatic bulb covered with the porous absorptive material being sized and configured to be withdrawn into the sheath by tension on the first end of the displaceable wire;
   the second end of the displaceable wire comprising a piston, a cellular sampling structure configured to disrupt a tissue surface to dislodge cells, and the porous absorptive material being configured to draw in and retain a fluid sample comprising cellular material, wherein the cellular sampling structure and the porous absorptive material are external to the sheath in the first state and the cellular sampling structure is internal to the sheath in the second state and the piston is proximal to the cellular sampling structure with respect to the porous absorptive material;
   the flexible coaxial structure being configured such that a tension on the first end of the displaceable wire at the proximal end of the sheath results in a retraction of the displaceable wire from the first state to the second state, to cause a displacement into the sheath of the displaceable wire and a corresponding proximal displacement of the piston, the cellular sampling structure, and the porous absorptive material, with suction of media external to the sheath into the distal end of the sheath, the porous absorptive material being configured to retain the fluid sample comprising cellular material obtained in the first state after transition to the second state,
   wherein the coaxial structure is configured to be inserted to a determined depth through an internal cervical os of a uterus of a human, to retrieve an endometrial biopsy sample, and to be withdrawn from the cervix.

2. The tissue sampling device according to claim 1, wherein the porous absorptive material in the second state and the sheath protect a biopsy sample within the sheath obtained during transition from the first state to the second state from contamination during withdrawal of the distal end from a patient.

3. The tissue sampling device according to claim 1, wherein the porous absorptive material is adapted for absorbing a biopsy sample for nucleic acid analysis.

4. The tissue sampling device according to claim 1, wherein the porous absorptive material is a sponge.

5. The tissue sampling device according to claim 1, wherein the cellular sampling structure comprises a brush.

6. The tissue sampling device according to claim 5, wherein the brush comprises a plurality of bristles extending radially from the displaceable wire.

7. The tissue sampling device according to claim 1, wherein the coaxial structure is further configured to be:
   inserted into the cervical os with the displaceable structure in the second state to a predetermined depth;
   extended into the first state with the cellular sampling structure within the uterus;
   manipulated by a user by movement of the first end of the displaceable structure to dislodge cells within the uterus;

retracted into the second state within the uterus, to cause the vacuum to withdraw a liquid sample surrounding the cellular sampling structure in to into the distal end of the sheath; and retracted from the cervical os with the displaceable structure in the second state.

8. The tissue sampling device according to claim 1, wherein the cellular sampling structure comprises a spirally twisted steel wire with bristles extending therefrom, welded to a proximal guidewire.

9. The tissue sampling device according to claim 8, wherein the porous absorptive material formed at the second end comprises a urethane foam provided over a cap terminating the spirally twisted steel wire.

10. The tissue sampling device according to claim 1, wherein the sheath has an outer diameter of between 1 and 3 mm, and a length between 20 and 50 cm.

11. The tissue sampling device according to claim 1, further comprising a slidable skirt stopper provided on an exterior surface of the flexible sheath, configured to prevent insertion of the flexible sheath within the uterus of a patient beyond an axial location of the skirt stopper.

12. The tissue sampling device according to claim 1, comprising:

at least two flexible coaxial structures, each having a respective sheath, a respective displaceable wire, a respective piston, a respective cellular sampling structure and a respective porous absorbent material; and a housing, configured to selectively engage and disengage a respective displaceable wire of a respective flexible structure to a user interface, such that when engaged, tension and compression are passed from the user interface to the displaceable structure to transition the displaceable structure between the first state and the second state, and when disengaged, tension and compression are not passed from the user interface to the displaceable structure.

13. The tissue sampling device according to claim 1, further comprising an electrical motor configured to move the displaceable structure.

14. A flexible coaxial tissue sampling device, comprising:

a sheath;

a displaceable wire within the sheath, the displaceable wire having a first end extending from a proximal end of the sheath and second end configured, in a first state, to extend from a distal end of the sheath, and in a second state, to retract into the distal end of the sheath;

the second end of the displaceable wire comprising a cellular sampling structure configured to disrupt a tissue surface to dislodge cells and an atraumatic bulb covered by a porous absorptive material configured to draw in and retain a fluid sample comprising cellular material, wherein the cellular sampling structure and the porous absorptive material are external to the sheath in the first state and the cellular sampling structure and the porous absorptive material are internal to the sheath in the second state;

the flexible coaxial structure being configured such that a tension on the first end of the displaceable wire at the proximal end of the sheath results in a retraction of the displaceable wire from the first state to the second state, to cause a displacement into the sheath of the displaceable wire and the cellular sampling structure, and a vacuum within the sheath to draw in a fluid sample from intrauterine fluid surrounding the distal end of the sheath, the porous absorptive material being configured to retain the fluid sample comprising cellular material obtained in the first state after transition to the second state and to protect tissue from contact with the second end of the displaceable wire, wherein the flexible coaxial structure is configured to be inserted to a determined depth through an internal cervical os of a uterus of a human, to retrieve an endometrial biopsy sample, and to be withdrawn from the cervix.

15. The flexible coaxial tissue sampling device according to claim 14, wherein the cellular sampling structure comprises a brush having a plurality of radially extending bristles from the displaceable wire and terminating in the atraumatic bulb covered by the porous absorptive material, the porous absorptive material comprising an open cell foam;

further comprising a piston displaceable with the displaceable wire and proximal to the cellular sampling structure with respect to the porous absorptive material, configured to create a negative pressure within the sheath distal to the piston when the displaceable wire is withdrawn into the sheath.

16. A biopsy method, comprising:

providing the flexible coaxial tissue sampling device according to claim 14;

inserting the distal end of the sheath through a cervix, past the internal cervical os, into a uterus, while the flexible coaxial structure is in the second state;

pushing the first end of the displaceable wire into the sheath, to cause the flexible coaxial tissue sampling device to assume the first state;

manipulating the displaceable wire to obtain a cellular sample with the cellular sampling structure rubbing against the endometrium and the porous absorptive material absorbing the fluid comprising cellular material while protecting the endometrium from intrusion by a tip of the displaceable wire; and applying a tension on the first end of the displaceable wire at the proximal end of the sheath to cause a retraction of the displaceable wire from the first state to the second state, and consequent withdrawal of the displaceable wire, the cellular sampling structure, and the porous absorptive material into the sheath, while retaining the absorbed fluid in the porous absorptive material; and withdrawing the distal end of the sheath with the porous absorptive material within the sheath to prevent contamination of a biopsy sample retained on the cellular sampling structure and the porous absorptive material by cells within the cervix and vagina.

17. The flexible coaxial tissue sampling device according to claim 14, wherein:

the porous absorptive material in the second state and the sheath protect a biopsy sample within the sheath proximal to the porous absorptive material, obtained during transition from the first state to the second state from contamination during withdrawal of the distal end from a patient, the porous absorptive material is a sponge adapted for absorbing a biopsy sample for nucleic acid analysis; and the cellular sampling structure comprises a brush comprising a plurality of bristles extending radially from the displaceable wire.

18. The flexible coaxial tissue sampling device according to claim 14, wherein the displaceable wire within the sheath is further configured to be:

inserted into the internal cervical os with the displaceable wire in the second state to a predetermined depth;

extended into the first state with the cellular sampling structure within the uterus;

manipulated by a user by movement of the first end of the displaceable wire to dislodge cells within the uterus;

retracted into the second state within the uterus, to cause the vacuum to draw in the fluid sample from the intrauterine fluid surrounding the distal end of the sheath into the distal end of the sheath; and retracted from the internal cervical os and vagina with the displaceable structure in the second state.

19. The flexible coaxial tissue sampling device according to claim 14, wherein:

the displaceable wire comprises proximal guidewire welded to the cellular sampling structure comprising a spirally twisted steel wire with bristles extending therefrom;

the porous absorptive material comprises a urethane foam provided over the atraumatic bulb terminating the spirally twisted steel wire; and the sheath has an outer diameter of between 1 and 3 mm, and a length between 20 and 50 cm.

20. The flexible coaxial tissue sampling device according to claim 14, further comprising a skirt stopper provided on an exterior surface of the flexible sheath, configured abut to the cervix to limit insertion depth of the sheath.

* * * * *